(12) United States Patent
Eudes et al.

(10) Patent No.: US 11,434,498 B2
(45) Date of Patent: Sep. 6, 2022

(54) BIOLOGICAL NITROGEN FIXATION IN CROPS

(71) Applicant: Her Majesty The Queen in Right of Canada, as Represented by the Minister of Agriculture and Agri-Food, Lethbridge (CA)

(72) Inventors: François Eudes, Lethbridge (CA); Alicja Ziemienowicz, Lethbridge (CA)

(73) Assignee: HER MAJESTY THE QUEEN IN RIGHT OF CANADA, AS REPRESENTED BY THE MINISTER OF AGRICULTURE AND AGRI-FOOD, Lethbridge (CA)

(*) Notice: Subject to any disclaimer, the term of this patent is extended or adjusted under 35 U.S.C. 154(b) by 0 days.

(21) Appl. No.: 16/962,376

(22) PCT Filed: Jan. 10, 2019

(86) PCT No.: PCT/CA2019/050038
§ 371 (c)(1),
(2) Date: Jul. 15, 2020

(87) PCT Pub. No.: WO2019/140509
PCT Pub. Date: Jul. 25, 2019

(65) Prior Publication Data
US 2021/0062210 A1 Mar. 4, 2021

Related U.S. Application Data

(60) Provisional application No. 62/619,949, filed on Jan. 22, 2018.

(51) Int. Cl.
*C12N 15/82* (2006.01)
*C12N 15/87* (2006.01)
*C12N 9/02* (2006.01)

(52) U.S. Cl.
CPC ....... *C12N 15/8261* (2013.01); *C12N 9/0095* (2013.01); *C12N 15/8221* (2013.01); *C12Y 118/06001* (2013.01)

(58) Field of Classification Search
None
See application file for complete search history.

(56) References Cited

U.S. PATENT DOCUMENTS

| | | | |
|---|---|---|---|
| 8,470,972 B2 | 6/2013 | Khan | |
| 2011/0124073 A1 | 5/2011 | Devroe et al. | |
| 2014/0011261 A1 | 1/2014 | Wang et al. | |
| 2014/0196172 A1* | 7/2014 | Eudes | C12N 15/8221 800/278 |
| 2014/0196178 A1 | 7/2014 | Zaltsman | |
| 2016/0304842 A1* | 10/2016 | Donovan | C12Y 118/06001 |

FOREIGN PATENT DOCUMENTS

| | | |
|---|---|---|
| WO | 2008148223 A1 | 12/2008 |
| WO | 2009062713 A1 | 5/2009 |
| WO | 2013016810 A1 | 2/2013 |
| WO | 2015036419 A1 | 3/2015 |
| WO | 2015171494 A1 | 11/2015 |
| WO | 2018014130 A1 | 1/2018 |

OTHER PUBLICATIONS

Chuah, et al. (Scientific reports 5.1 (2015): 1-7) . (Year: 2015).*
Allen, R., et al., "Expression of 16 Nitrogenase Proteins within the Plant Mitochondrial." Frontiers in Plant Science, Mar. 2017, 8(287): 1-14.
Buren, S., et al., "State of the Art in Eukaryotic Nitrogenase Engineering." FEMS Microbiology Letters, 2018, 365(2): 1-9.
Curatti, L., et al., "Challenges to Develop Nitrogen-Fixing Cereals by Direct Nif-Gene Transfer." Plant Science, 2014, 225: 130-137.
Ivleva, N., et al., "Expression of Active Subunit of Nitrogenase via Integration into Plant Organelle Genome." PLos One, 2016, 11(8): e0160951, pp. 1-13.
Macmillan, T., et al., "Gene Delivery into the Plant Mitochondria Via Organelle-Specific Peptides." Plant Biotechnology Reports, 2019, 13: 11-23.
Macmillan, T., "Plant Organelle Targeting Cell Penetrating Peptides (Doctoral Dissertation)." University of Lethbridge, Dept. of Biological Sciences, 2014: http://hdl.handle.net/10133/3543, pp. i-131.
Oldroyd, G., et al., "Biotechnological Solutions to the Nitrogen Problem." Current Opinion in Biotechnology, 2014, 26: 19-24.
Temme, K., et al., "Refactoring the Nitrogen Fixation Gene Cluster from Klebsiella Oxytoca." Proceedings of the National Academy of Sciences, May 2012, 109(18): 7085-7090.
Ziemienowicz, A., et al., "Applications of CPPs in Genome Modulation of Plants." Methods in Molecular Biology, 2015, 1324: 417-434.

* cited by examiner

*Primary Examiner* — Charles Logsdon
(74) *Attorney, Agent, or Firm* — Saliwanchik, Lloyd & Eisenschenk

(57) ABSTRACT

A method of transforming a mitochondrion of a plant cell to express a nitrogenase enzyme includes exposing the plant cell to a mitochondrial-targeting nanocarrier polypeptide and one or more nucleic acids encoding the nitrogenase enzyme. The one or more genes encoding the nitrogenase enzyme can be one or more *Klebsiella* nif genes. The method can be used to generate plants which have the capability of fixing atmospheric elemental nitrogen.

12 Claims, 14 Drawing Sheets
Specification includes a Sequence Listing.

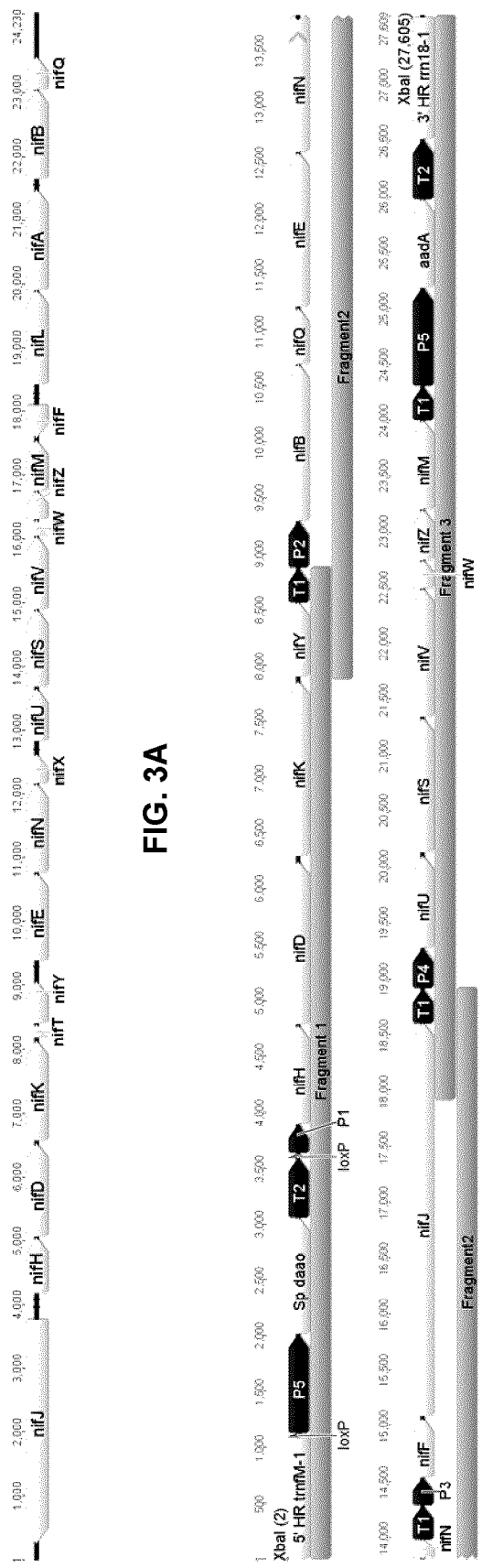
FIG. 3A
FIG. 3B
FIG. 3C

BIOLOGICAL NITROGEN FIXATION IN CROPS

CROSS REFERENCE TO RELATED APPLICATIONS

This application is a National Stage of International Application No. PCT/CA2019/050038, filed on Jan. 10, 2019; which claims the benefit of U.S. Provisional Application Ser. No. 62/619,949, filed Jan. 22, 2018, both of which are hereby incorporated by reference in their entirety.

SEQUENCE LISTING

The Sequence Listing for this application is labeled "SeqList-ST25.txt," which is 9 KB. The Sequence Listing is incorporated herein by reference in its entirety.

BACKGROUND

The present application is directed to a method of genetically engineering a plant to be capable of fixing atmospheric elemental nitrogen (dinitrogen; $N_2$). More specifically, the present application is directed to a method of genetically transforming a mitochondrion of a plant cell to express a nitrogenase enzyme.

A key element in increasing the productivity of cereal crops, including wheat, maize and rice, is the use of fertilizers, particularly nitrogen and phosphate fertilizers. More than half of the food currently consumed by the world population is produced using nitrogen fertilizers, which contribute to 40-60% of crop yield. However, production and uses of nitrogen fertilizers such as ammonia ($NH_3$) and urea ($NH_2CONH_2$) can have severe detrimental effects on the environment. The Haber-Bosch process for production of ammonia for fertilizer from elemental nitrogen ($N_2$) and hydrogen ($H_2$) requires a significant use of energy, often obtained from fossil fuels. Furthermore, overuse or inefficient use of nitrogen fertilizers can result in loss of excess fertilizer to the environment. The resulting eutrophication can lead to changes in biodiversity and reduction of water quality. In addition, denitrification of nitrogen fertilizer produces the greenhouse gas nitrous oxide ($N_2O$), which can contribute to global warming. Reducing the need for nitrogen fertilizer without loss of crop productivity would provide a benefit to both farmers and the environment.

Diazotrophic prokaryotic microorganisms can "fix" atmospheric $N_2$ by converting the $N_2$ to biologically useful nitrogen-containing compounds which can be assimilated by nearby plants. These microorganisms produce a multi-subunit nitrogenase (also known as dinitrogenase) metalloenzyme complex which catalyzes the reduction of $N_2$ to $NH_3$ and is sensitive to oxygen and dependent on high levels of ATP and reductant. Nitrogenase activity is encoded by a large number of highly conserved nif genes which are organised in operons. For example, twenty such genes are present in the bacteria *Klebsiella pneumoniae* and *Klebsiella oxytoca*.

The components of the nitrogenase enzyme complex itself are encoded by the genes nifH, nifD, nifK, and nifY. The genes nifD and nifK encode the alpha and beta subunits, respectively, of the heterotetrameric iron-molybdenum component (component I) of the dinitrogenase enzyme, while the nifH gene encodes the subunit of the homodimeric iron protein component (component II). The nifY gene encodes an iron molybdenum cofactor biosynthesis protein, which is initially associated with the apodinitrogenase oligomer but dissociates from the complex when the apodinitrogenase is activated by addition of the iron-molybdenum cofactor. Other nif genes are also involved in regulation, assembly, maturation and function of the dinitrogenase enzyme. Specifically, the genes nifE nifN, nifX, nifU, nifS, nifV, nifW, nifZ, nifM, nifB and nifQ are involved in cofactor biosynthesis, the genes nifJ and nifF are involved in electron transfer, and the genes nifL and nifA are involved in regulation of nif gene expression.

Various approaches have been considered to take advantage of biological nitrogen fixation so as to reduce dependence on nitrogen fertilizers in cultivation of cereal plants. One possible approach is to produce genetically engineered diazotrophs and/or cereal plants which can form symbiotic relationships, similar to the endosymbiotic relationships which certain diazotrophs, such as rhizobacteria, can form with certain plants, such as legumes, by invading the root tissue of the plant, colonizing the root nodules that form in response to the invasion, and providing benefits which promote plant growth, including releasing nitrogen-fixation products to be taken up by the plant. Another approach is to improve the efficiency of nitrogen-fixing bacterial endophytes which are naturally associated with cereals, such as certain species of *Azospirillum, Azoarcus* and *Herbaspirillum*. However, both of these approaches rely on the use of biofertilizer inoculants, the effectiveness of which may not be always reliable. In addition, even though nodulation-associated biochemical factors have been discovered in cereal plants, the role of these factors in cereal crops is not yet completely understood. An alternative approach is to engineer cereal plants to carry and express bacterial nif genes, thereby providing these plants with the ability to fix elemental atmospheric nitrogen themselves. However, this approach has so far been only partially successful.

Plastids and mitochondria are organelles offering potential subcellular locations for expression of nitrogenase. Both types of organelles could provide the ATP and electrons required for nitrogenase to function, although plastids and mitochondria differ in their internal $O_2$ levels and their ability to incorporate ammonium into amino acids. Other advantages of plant non-nuclear organelles over the nucleus as a subcellular location for nitrogenase expression include the bacterial origin of plastids and mitochondria, the small genome size within mitochondria and plastids, the abundance of genome copies and the presence of gene regulation mechanisms similar to those in bacteria. Moreover, there are no epigenetic effects or silencing in mitochondria or plastids, which results in reproducible and heritable protein accumulation.

Attempts to express nif genes in chloroplasts have been partially successful. However, mitochondria provide an environment with low oxygen levels and high energy content generated by catabolism to support the energy-demanding $N_2$ metabolic pathway, and are therefore potentially a suitable location for expression of nitrogenase. It is therefore desirable to provide a method of expressing nitrogenase genes within plant cell mitochondria.

SUMMARY

One aspect of the present invention provides a method of transforming a mitochondrion of a plant cell to express a nitrogenase enzyme, the method comprising exposing the plant cell to a mitochondrial-targeting nanocarrier polypeptide and one or more nucleic acids, wherein the one or more nucleic acids comprise one or more genes encoding the nitrogenase enzyme. In at least one embodiment, the one or more genes encoding the nitrogenase enzyme include one or more nif genes. In at least one embodiment, the one or more nucleic acids further comprise at least one selection marker gene.

In an additional aspect, the present invention provides a genetically engineered plant cell comprising a mitochondrion transformed by the method described herein. Further aspects of the present invention provide a genetically engineered plant comprising the genetically engineered plant cell and a method of generating a genetically engineered plant from the genetically engineered plant cell.

BRIEF DESCRIPTION OF THE DRAWINGS

Further features of the present invention will become apparent from the following written description and the accompanying figures, in which:

FIG. 3A is a schematic representation of the nif gene cluster found in *Klebsiella oxytoca*;

FIG. 3B is a schematic representation of a construct optimized for expression of the nif gene cluster in triticale and wheat mitochondria, including many of the nif genes of FIG. 3A in addition to the plant mitochondrial promoters P1 (Ta atpA; *Triticum aestivum* ATP synthase subunit alpha), P2 (Ta atp6; *Triticum aestivum* ATP synthase subunit 6), P3 (At atp6; *Arabidopsis thaliana* ATP synthase subunit 6), P4 (Nt atp6; *Nicotiana tabacum* ATP synthase subunit 6) and P5 (Ta coxII; *Triticum aestivum* cytochrome c oxidase subunit II) and the terminator sequences T1 (Nt atp6; *Nicotiana tabacum* ATP synthase subunit 6) and T2 (Ta cobA; *Triticum aestivum* cytochrome B) (ribosome binding sites (RBS) and intergenic expression elements (IEEs) are not indicated). Sp daao represents the daao (D-amino acid oxidase) gene from *Saccharomyces pombe*, aadA represents the streptomycin 3'-adenylyltransferase gene from *Escherichia coli*, and 5'HR trnfM-1 and 3'HR rrn18-1 represent sequences homologous to the trnfM-1 gene (formylmethionine transfer RNA) region and the rrn18-1 gene (18S ribosomal RNA), respectively, of the wheat mitochondrial repeat regions;

FIG. 3C is a schematic representation of the wheat mitochondrial W_M_DAAO construct, in which P5, T2, Sp daao, 5'HR trnfM-1 and 3'HR rrn18-1 are the same elements as those indicated in the construct of FIG. 3B;

BRIEF DESCRIPTION OF SEQUENCES

Figure 1A:
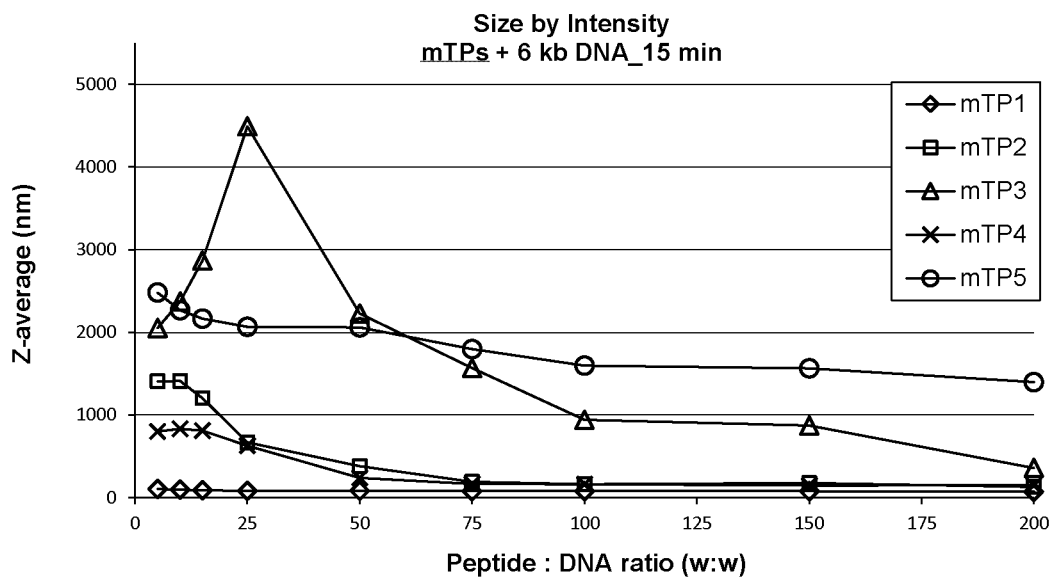
FIG. 1A is a graph showing the Z-average size of nanocomplexes formed by incubating various mitochondrial-targeting peptides (mTPs) with 6 kilobase pair (kb) linear DNA at various ratios of peptide to DNA by weight for 15 minutes.

SEQ ID NOs: 1-47 are sequences useful according to the subject invention.

DETAILED DESCRIPTION

The present application describes a method of transforming a mitochondrion of a plant cell to express a nitrogenase enzyme, and a plant cell containing a mitochondrion transformed by the method to express the nitrogenase enzyme. Suitable plant cells are cells of plant species including but not limited to grass plants and cereal crops (including but not limited to triticale, wheat, barley, buckwheat, canary seed, fescue, foxtail, maize, millet, oat, rye, rice, sorghum, sugarcane and timothy), oilseed plants or crops (including but not limited to *Arabidopsis*, canola, peanut, rape, flax, sunflower, soybean and safflower) and other non-legume crops (including but not limited to cotton, tobacco, vegetables and fruit plants). In at least one embodiment, the plant cell is a triticale cell. In at least one embodiment, the plant cell is a wheat cell. In at least one embodiment, the plant cell is a microspore. Other suitable plant cells are well known in the art.

The method of transforming the mitochondrion of the plant cell includes exposing the plant cell to a mitochondrial-targeting nanocarrier polypeptide and one or more nucleic acids. In at least one embodiment, the mitochondrial-targeting nanocarrier polypeptide is a polypeptide which is effective to mediate the transport of a nucleic acid into a plant cell and into a mitochondrion within the plant cell. Examples of such polypeptides are described in international patent application publication WO 2013/016810 and can be readily identified and prepared by the skilled person. In at least one embodiment, the mitochondrial-targeting nanocarrier polypeptide is:

```
mTP1
                                        (SEQ ID NO: 1)
MFSYLPRYPLRAASARALVRATRPSYRSALLRYQ mTP2
                                        (SEQ ID NO: 2)
MAAWMRSLFSPLKKLWIRMH mTP3
                                        (SEQ ID NO: 3)
MKLLWRLILSRKW mTP4
                                        (SEQ ID NO: 4)
MWWRRSRTNSLRYT
or mTP5
                                        (SEQ ID NO: 5)
MLFRLRRSVRLRGLLA.
```

According to the present method, the one or more nucleic acids comprise one or more genes encoding a nitrogenase enzyme. In at least one embodiment, the nitrogenase enzyme is an enzyme or complex thereof effective to reduce elemental dinitrogen (N$_2$) to ammonia (NH$_3$). In at least one embodiment, the nitrogenase enzyme is encoded by one or more genes originating from a species of bacteria. In at least one embodiment, the species of bacteria is a diazotrophic species, including but not limited to species of *Klebsiella, Rhizobium, Clostridium, Azotobacter, Anabaena, Nostoc* and *Rhodobacter*. In at least one embodiment, the species of bacteria is a species of *Klebsiella*. Other suitable sources of genes encoding nitrogenase enzymes will be apparent to those skilled in the art.

In at least one embodiment, the nitrogenase enzyme is encoded by one or more nif genes. In at least one embodiment, the nif genes include but are not limited to nifH, nifD and nifK. In at least one embodiment, the nif genes include but are not limited to nifH, nifD, nifK and nifY. In at least one embodiment, the nif genes further include one or more of nifE nifN, nifU, nifS, nifV, nifW, nifZ, nifM, nifB, nifQ, nifJ and nifF. In at least one embodiment, the nif genes further include one or more of nifE nifN, nifX, nifU, nifS, nifV, nitW, nitZ, nifM, nifB, nifQ, nifJ, nifF, nifL and nifA.

In at least one embodiment, the one or more nif genes are located on a single nucleic acid fragment. In at least one embodiment, the one or more nif genes are located on two or more nucleic acid fragments. In at least one embodiment, the nifH, nifD, nifK and nifY genes are located on a single nucleic acid fragment. In at least one embodiment, the nifB, nifQ, nifE, nifN, nifF and nifJ genes are located on a single nucleic acid fragment. In at least one embodiment, the nifU, nifS, nifV, nitW, nifZ and nifM, genes are located on a single nucleic acid fragment. In at least one embodiment, the nucleic acid fragments also contain regulatory elements, including but not limited to promoters, terminators, ribosome binding sites, intergenic expression elements and repeat regions, effective to control one or more of replication, transcription and translation of the nif genes in plant mitochondria. Such regulatory elements are known and can be identified and used by the person of skill in the art in light of the teaching herein to design a nucleic acid construct active to express nif genes in plant mitochondria.

In at least one embodiment, the one or more nucleic acids are introduced into the mitochondria of the plant cell by exposing the plant cell to the one or more nucleic acids and the mitochondrial targeting nanocarrier polypeptides under conditions under which the nucleic acids enter into the cell and into the mitochondria within the cell. In at least one embodiment, the mitochondrial targeting nanocarrier polypeptide and DNA are mixed to form a nanocomplex to which the plant cell is exposed. In at least one embodiment, the ratio by weight (w/w) of mitochondrial targeting nanocarrier polypeptide to nucleic acid in the nanocomplex is from about 2.5:1 to about 200:1. In at least one embodiment, the ratio by weight (w/w) of mitochondrial targeting nanocarrier polypeptide to nucleic acid in the nanocomplex is from about 5:1 to about 16:1. In at least one embodiment, the ratio by weight (w/w) of mitochondrial targeting nanocarrier polypeptide to nucleic acid in the nanocomplex is about 15:1. In at least one embodiment, the ratio by weight (w/w) of mitochondrial targeting nanocarrier polypeptide to nucleic acid in the nanocomplex is about 100:1. The skilled person will be readily able, in light of the teaching herein, to determine other possible conditions under which the plant cell can be exposed to the one or more nucleic acids and the mitochondrial targeting nanocarrier polypeptides such that the nucleic acids enter into the cell and into the mitochondria within the cell.

In at least one embodiment, the one or more nucleic acids further comprise at least one selection marker gene. As used herein, the term "selection marker gene" is intended to refer to a gene which, when present in a transgenic cell or organism, including but not limited to a transgenic plant or plant cell, can be expressed to provide the transgenic cell or organism with a specific detectable trait or phenotype. In this way, it is possible to distinguish an organism possessing the gene from one which does not possess the gene. In certain embodiments, the selection marker gene can also selectively permit only those cells or organisms containing the gene to survive or grow under certain conditions. In this way, it is possible to selectively generate a population of cells or organisms containing the gene under conditions where otherwise similar or identical cells or organisms not containing the gene may fail to survive or grow. If the selection marker gene is located on the same nucleic acid as another gene, the presence of the selection marker gene in a cell or organism can indicate the presence of the other gene in the cell or organism as well. Such selection marker genes are well known in the art and can be readily selected and utilized by the skilled person.

In at least one embodiment, the selection marker gene is suitable for transformation of the genome of a non-nuclear organelle within a cell, including but not limited to the genome of a mitochondrion or a chloroplast. In at least one embodiment, the selection marker gene is suitable for expression in a non-nuclear organelle, including but not limited to a mitochondrion or a chloroplast.

In at least one embodiment, the selection marker gene is an *Escherichia coli* streptomycin 3"-adenylyltransferase gene, also represented as aadA. Embryogenesis of untransformed microspores lacking this gene is inhibited in the presence of the antibiotic streptomycin. In contrast, the enzyme expressed by the aadA gene catalyzes the adenylylation of streptomycin, protecting transgenic plant microspores incorporating this gene from the deleterious effects of streptomycin. Thus, when cultured or germinated in the presence of streptomycin, transgenic microspores expressing the aadA gene, or embryos generated therefrom, are expected to have a survival advantage over microspores and embryos which do not express the gene.

In at least one embodiment, the selection marker gene is a *Saccharomyces pombe* D-amino acid oxidase gene, also represented as daao. Embryos originating from untransformed microspores lacking this gene have a reduced ability to germinate and form healthy plantlets when embryogenesis and/or germination takes place in the presence of D-alanine (D-Ala). However, the enzyme expressed by the daao gene catalyzes the oxidation of D-alanine, protecting transgenic plant cells or tissues, including but not limited to embryos, which incorporate this gene from the deleterious effects of D-alanine. Thus, when cultured or germinated in the presence of D-alanine, embryos generated from transgenic microspores expressing the daao gene are expected to have a survival advantage over embryos generated from microspores which do not express the gene.

In a further aspect, the present application describes methods of producing a genetically engineered plant from a plant cell containing mitochondria capable of expressing a nitrogenase enzyme as described herein, and genetically engineered plants produced by such methods. Such methods of producing genetically engineered plants from genetically engineered plant cells, including but not limited to microspores, are well known in the art, and include, but are not limited to, embryogenesis and in vitro plant regeneration techniques.

As used herein, the terms "about" or "approximately" as applied to a numerical value or range of values are intended to mean that the recited values can vary within an acceptable degree of error for the quantity measured given the nature or precision of the measurements, such that the variation is considered in the art as equivalent to the recited values and provides the same function or result. For example, the degree of error can be indicated by the number of significant figures provided for the measurement, as is understood in the art, and includes but is not limited to a variation of ±1 in the most precise significant figure reported for the measurement. Typical exemplary degrees of error are within 20 percent (%), preferably within 10%, and more preferably within 5% of a given value or range of values. Alternatively, and particularly in biological systems, the terms "about" and "approximately" can mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

As used herein, the term "substantially" refers to the complete or nearly complete extent or degree of an action, characteristic, property, state, structure, item, or result. For example, an object that is "substantially" aligned would mean that the object is either completely aligned or nearly completely aligned. The exact allowable degree of deviation from absolute completeness may in some cases depend on the specific context. However, generally speaking the nearness of completion will be so as to have the same overall result as if absolute and total completion were obtained.

The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

EXAMPLES

Other features of the present invention will become apparent from the following non-limiting examples which illustrate, by way of example, the principles of the invention.

Example 1

Characterization of mTP-DNA Nanocomplexes

Peptides

Mitochondrial targeting nanocarrier polypeptides (mTPs) 1-5, described in international patent application publication WO 2013/016810, were synthesized by CanPeptide Inc. Canada. The sequences of mTPs 1 to 5 are provided below.

```
mTP1
                                          (SEQ ID NO: 1)
MFSYLPRYPLRAASARALVRATRPSYRSALLRYQ mTP2
                                          (SEQ ID NO: 2)
MAAWMRSLFSPLKKLWIRMH mTP3
                                          (SEQ ID NO: 3)
MKLLWRLILSRKW mTP4
                                          (SEQ ID NO: 4)
MWWRRSRTNSLRYT mTP5
                                          (SEQ ID NO: 5)
MLFRLRRSVRLRGLLA
```

The five mTPs were tested for their ability to non-covalently bind to nucleic acids, a property needed to translocate double stranded DNA (dsDNA) molecules. A gel mobility shift assay and a nuclease protection assay were separately performed with each peptide to determine the minimum amount of peptide needed to bind to and completely saturate the linearized dsDNA in preparation for microspore transfections.

Gel Shift Assay

One μg of linear double-stranded plasmid DNA (pDNA, 6.0 kb) was mixed with increasing amounts (from 0 to 20μg) of each of the five mTPs in individual reaction mixtures (50μL total volume), and the reaction mixture was incubated for 15 minutes, and then subjected to electrophoresis on a 0.8% agarose gel stained with ethidium bromide.

A complete shift in DNA mobility caused by the peptides was observed at the weight-to-weight peptide:DNA binding ratio of 2.5:1 to 8:1.

DNase Protection Assay mTPs 1-5 were separately mixed with pDNA as described for the gel shift assay above. 5μl of DNase I (RNase-free DNase set; Qiagen, Valencia, Calif., USA) was added to the mixture volume (50μl). The mixture was incubated at room temperature for 15 minutes and then incubated on ice for 5 min. Plasmid-peptide dissociation and plasmid purification were carried out with a commercially available DNA purification kit (QIAquick™ PCR purification kit; Qiagen). DNA was eluted in sterile water and subjected to 0.8% agarose gel electrophoresis.

All of the mTPs were found to be able to protect DNA from nuclease degradation at the peptide:DNA ratios ~2 fold higher than that required for a gel shift. The optimal peptide: DNA ratios were: 5:1, 12:1, 8:1, 15:1 and 16:1 for mTP1, mTP2, mTP3, mTP4 and mTP5, respectively.

Zeta-Sizer Analysis mTP-DNA complexes were formed as described above for the gel mobility shift assay. Size analysis of a 20μL sample was carried out immediately after incubation in low volume quartz sizing cuvette (ZEN 2112) on a Zetasizer™ Nano ZS (Malvern) with a 633 nm laser at 173° backscatter. Data was analyzed using the CONTIN algorithm in the Zetasizer™ software v.7.02 (Malvern). Three repeat measurements were made of each sample and means and standard deviations of both the primary particle size distribution peak and the polydispersity index (PDI) were calculated and plotted. As used herein, the term "polydispersity index" or "PDI" is intended to mean a parameter calculated from data obtained from a dynamic light scattering experiment carried out on a sample containing sub-micrometer sized particles dispersed in a medium. The value of the polydispersity index indicates the degree of heterogeneity of the sizes of the particles in the sample subjected to the experiment. Calculation of polydispersity index can be carried out as described in ISO standard 22412:2017, revising ISO standards 22412: 2008 and 13321:1996.

The zeta-potential of the remaining sample (80μL) samples was read using a capillary zeta-cuvette with gold electrodes in a Zetasizer™-Nano (Malvern). The samples were prepared to a volume of 700μL to fill the cuvette. As used herein, the term "zeta-potential" is intended to refer to the electrostatic potential difference between the stationary layer of fluid around a particle dispersed in a dispersion medium and a point in the bulk dispersion medium away from the slipping plane or interface between the particle and the medium. Zeta potential is a measure of the electrostatic repulsion between nanoparticles bearing similar charges which are dispersed in a medium.

Figure 1B:
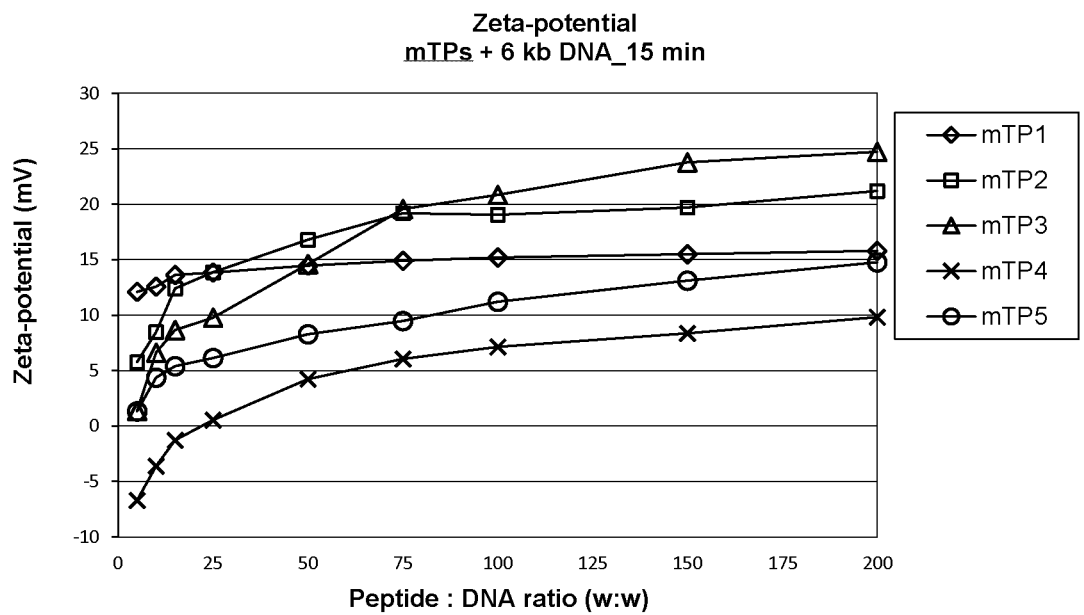
FIG. 1B is a graph showing the Zeta-potential of the nanocomplexes of FIG. 1A.
Figure 1C:
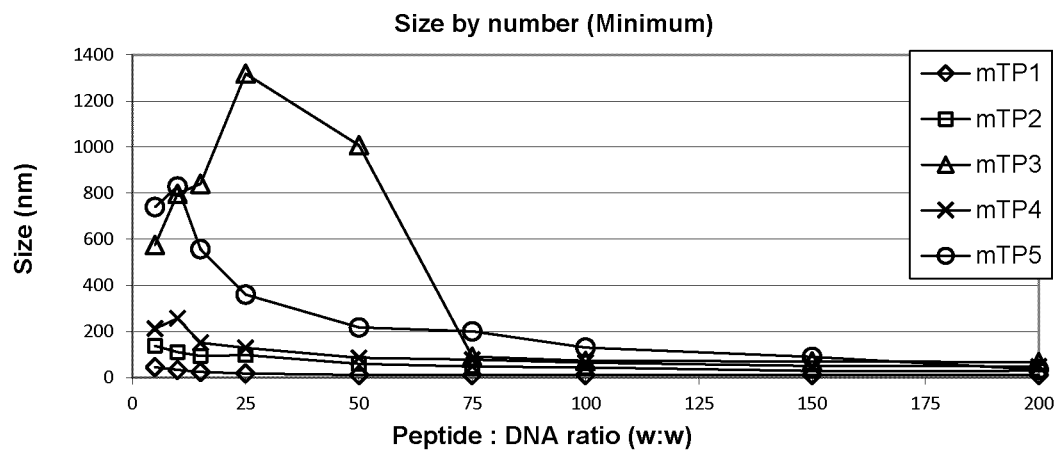
FIG. 1C is a graph showing the minimum size by number of the nanocomplexes of FIG. 1A.
Figure 1D:
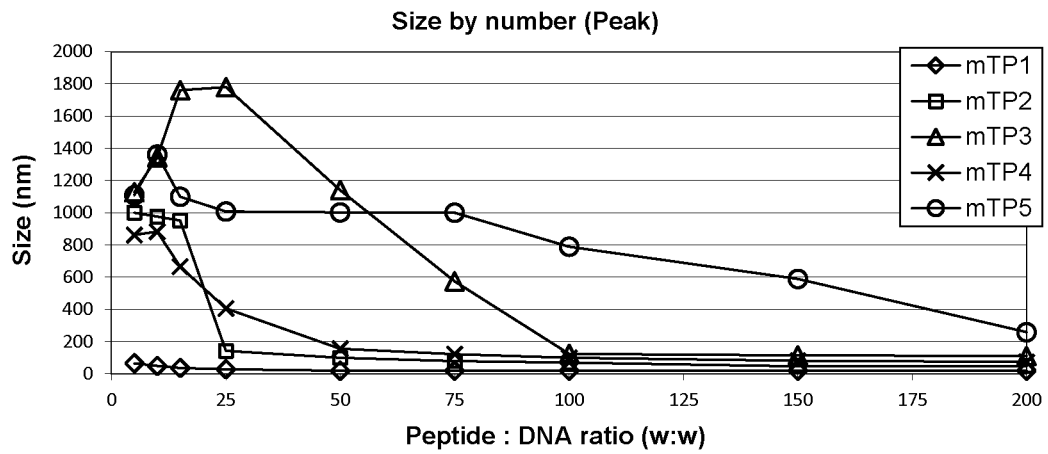
FIG. 1D is a graph showing the peak size by number of the nanocomplexes of FIG. 1A.
Figure 1E:
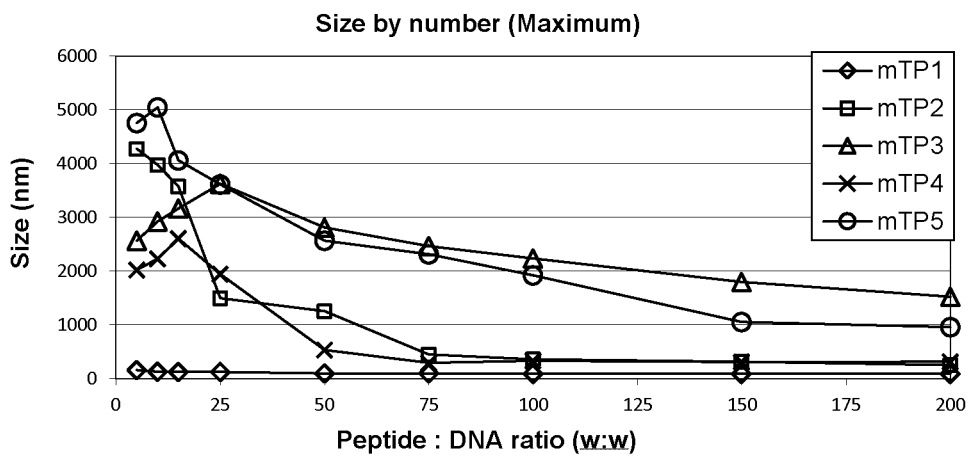
FIG. 1E is a graph showing the maximum size by number of the nanocomplexes of FIG. 1A.

The mTP-DNA nanocomplex size and charge was determined on complexes formed by mTPs with a 6.0 kb long linear DNA at various peptide:DNA ratios ranging from 5:1 to 200:1 by weight. As seen from the results presented in FIGS. 1A and 1B, at low peptide:DNA ratios, only mTP1 formed small complexes (FIG. 1A) with the highest Zeta-potential (FIG. 1B). Moreover, increasing the peptide:DNA ratio to ≥100:1 by weight resulted in a dramatic decrease in the complex size, especially for peptides mTP2, mTP3 and mTP4, and in an increase in the nanocomplex charge. As seen from the results presented in FIGS. 1C, 1D and 1E, another way of expressing the nanocomplex dimension, size by number, showed that the nanocomplexes formed with mTP2-5 range widely in size including a fraction of relatively small complexes (<100 nm) at high peptide:DNA ratios greater than 100:1 by weight. Generally, mTP1, mTP2 and mTP4 formed the smallest complexes with DNA.

Figure 1F:
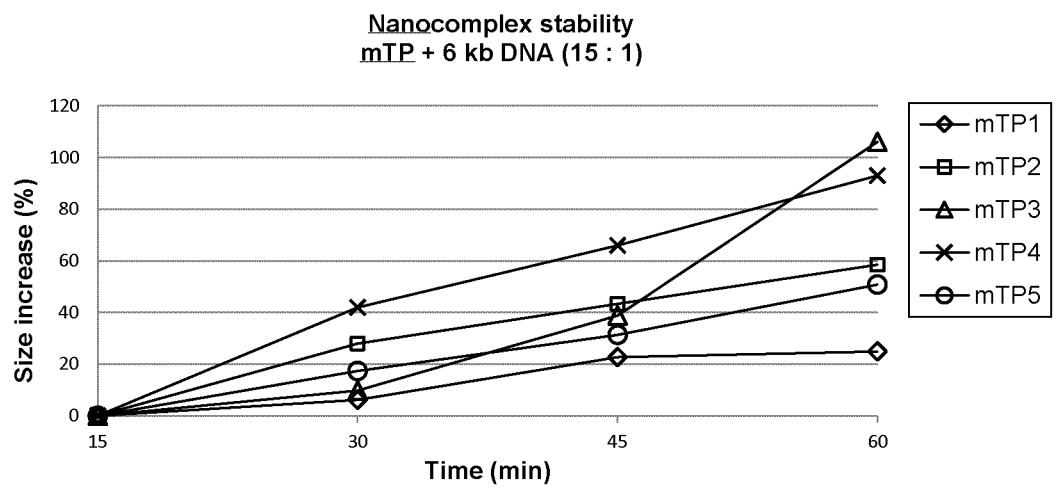
FIG. 1F is a graph showing the stability of the nanocomplexes of FIG. 1A prepared by incubation at a 15:1 by weight ratio of peptide to DNA for 15 minutes, determined by performing Z-sizer analyses in 15-minute intervals.
Figure 1G:
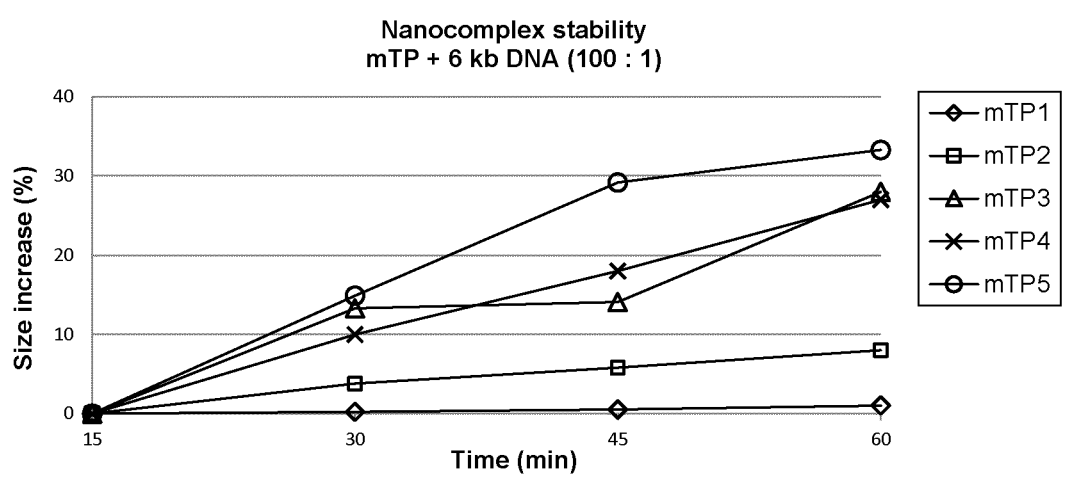
FIG. 1G is a graph showing the stability of the nanocomplexes of FIG. 1A prepared at a 100:1 by weight ratio of peptide to DNA, determined by performing Z-sizer analyses in 15-minute intervals.

Additionally, as seen from the results presented in FIGS. 1F and 1G, it was observed that the nanocomplexes produced with mTP2-5 at high peptide:DNA ratios were more stable than those created at lower ratios. At 15:1 peptide: DNA ratio by weight, complexes formed by mTP2, 3, 4 and 5 were unstable and tended to aggregate (increase in size by 50-100%; FIG. 1F), whereas at 100:1 peptide:DNA ratio by weight, these complexes are more stable (increase in size by 10-30%; FIG. 1G). The mTP1 peptide was different than the mTP2-5 peptides, because it formed small and very stable complexes with DNA at even the lowest peptide:DNA ratios (FIGS. 1A and 1C-1G).

Figure 2A:
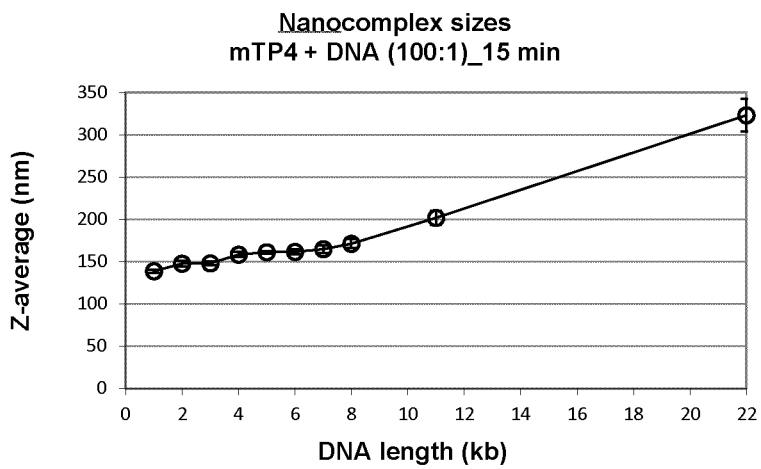
FIG. 2A is a graph showing the Z-average size of nanocomplexes generated by incubating DNA of various sizes (1-8 kb long linear DNA or 11 or 22 kb plasmid DNA) with mTP4 at a peptide:DNA ratio of 100:1 by weight for 15 minutes.
Figure 2B:
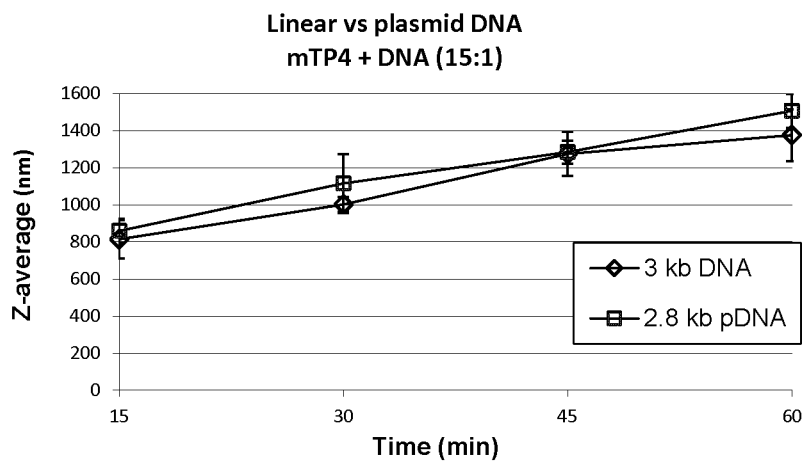
FIG. 2B is a graph showing the Z-average size of nanocomplexes generated by incubating 3 kb long linear DNA or 2.8 kb plasmid DNA with mTP4 at a peptide:DNA ratio of 15:1 by weight for 15 minutes, and performing Z-sizer analyses in 15 minute intervals.
Figure 2C:
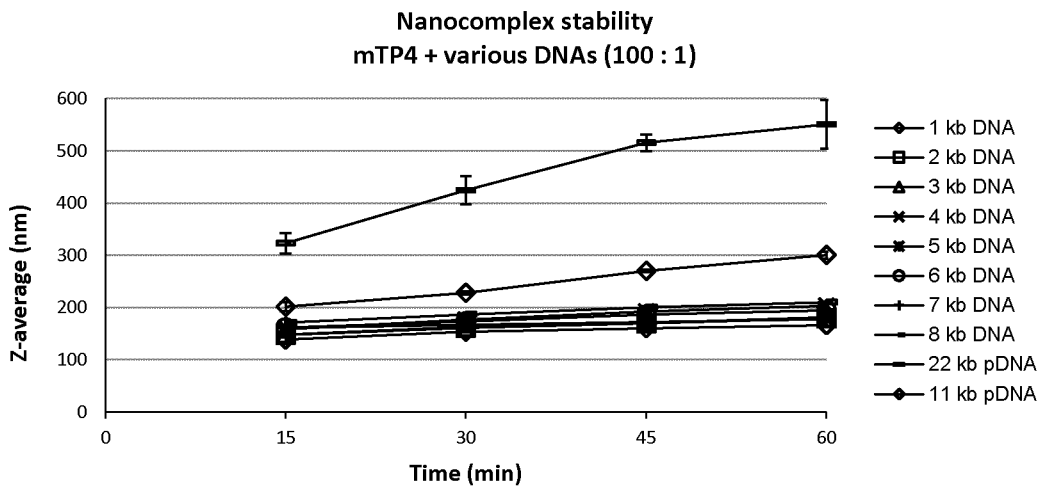
FIG. 2C is a graph showing the stability of the nanocomplexes of FIG. 2A.

The mTP4 peptide was used to study nanocomplexes formed with DNA of various sizes and forms. Since the entire nif gene cluster exceeds 20 kb in length while its operons vary in length from 4 kb to 10 kb, a broad range of DNA sizes (1-22 kb) were tested. As seen from the results presented in FIGS. 2A and 2C, it was observed that complexes formed by mTP4 with 1-8 kb long DNA at the same peptide:DNA ratio (100:1) showed similar size (~150 nm, FIG. 2A) and stability (increase in size by 10-30%; FIG. 2C). Increase in the complex size and instability was noticed for longer DNA (11 kb and 22 kb), which was particularly pronounced for the 22 kb long DNA molecules.

In order to test if the form of DNA has any effect on the size of nanocomplexes, a low (15:1) peptide:DNA ratio was used, because the complex size at this ratio was relatively large (~800 nm), thus allowing the observation of potential changes resulting from the more compact structure of plasmid DNA. However, as seen from the results presented in FIGS. 2B and 2C, nanocomplexes formed by mTP4 with linear and plasmid DNA showed similar size (FIG. 2B) and stability (FIG. 2C).

Example 2

Transfection of Triticale Microspores

Nif Construct Design and Synthesis

The nif gene cluster for expression in wheat/triticale mitochondria was designed using Geneious™ software. The nif construct was designed to comprise four nif operons adjusted for expression in wheat/triticale mitochondria by codon-usage optimization, replacement of nif operon promoters/terminators with plant mitochondrial gene expression regulatory elements and elimination of the bacterial regulatory genes. A schematic illustration of the construct is shown in FIG. 3B. In addition, the nif cluster is accompanied by two selectable marker genes (daao (D-amino acid oxidase) and aadA (streptomycin 3'-adenylyltransferase)) and flanked by 1 kb sequences homologous to the trnfM-1 and rrm18-1 genes of the wheat mitochondrial repeat regions.

Because of the better characteristics of nanocomplexes formed by mTPs with DNA shorter than 10 kb, it was decided to split the nif cluster (27.6 kb) into three (9-10 kb) fragments (Fragments 1, 2 and 3, respectively, as seen in FIG. 3B), containing 1 kb sequence overlaps. Fragments 1, 2 and 3 of the nif cluster were synthesized by Life Technologies (GeneArt) DNA synthesis service and delivered as pOA_nifclusterfrag1, pMK-V-Bs_nifclusterfrag2 and pMK-RQ_nifclusterfrag3 plasmids, respectively.

Microspore Isolation

Microspores were extracted from triticale (*Triticosecale* sp. *Whittmack* cv Sunray) plants using a modified version of a previously published extraction protocol (Asif et al., *Plant Cell Tissue Org. Cult.* (2013), 116(1): 125-130). Briefly, tillers were cut from donor plants at the early to mid uninucleate stage of microspore development, wrapped in aluminum foil and the stems were immersed in distilled water at 4° C. for 21±1 days. Glumes were removed and florets were harvested from nine tillers, placed in a Waring™ blender cup (VWR international, #58983-093) with 50 mL extraction buffer (13.4 mM $KNO_3$, 1.8 mM $(NH_4)_2SO_4$, 1.5 mM $KH_2PO_4$, 0.56 mM $CaCl_2$, 0.38 mM $MgSO_4$, 0.1 mM $FeSO_4$, 0.1 mM $Na_2EDTA$ (Ethylenediaminetetraacetic acid), 89.6µM MES hydrate (4-Morpholineethanesulfonic acid) and 400 mM mannitol, adjusted to pH 6.5 with KOH) and blended for two bursts of 7 s on low speed (18,000 rpm). The homogenate was then strained through autoclaved mesh (1 $mm^2$ pores) and the blender cup was rinsed with additional 50 mL of extraction buffer, followed by straining. The combined strain was filtered through 100µm sterile mesh (VWR international, #CA21008-950) into a 50 mL Falcon™ tube. Microspores were pelleted at 100×g for 5 minutes at 4° C., and the supernatant was decanted. The cells were then re-suspended in 15 mL of CIMC (Cereal Isolated Microspore Culture) wash (13.4 mM $KNO_3$, 1.8 mM $(NH_4)_2SO_4$, 1.5 mM $KH_2PO_4$, 0.56 mM $CaCl_2$, 0.38 mM $MgSO_4$, 2.4µM KI, 29.6µM $MnSO_4$, 80.9µM $H_3BO_3$, 17.4µM $ZnSO_4$, 52.5 nM $CoCl_2$, 50 nM $CuSO_4$, 52 nM $Na_2MoO_4$, 0.1 mM $FeSO_4$, 0.1 mM $Na_2EDTA$, 89.6µM MES hydrate, 14.8µM thiamine, 2.43µM pyridoxine, 4.06µM nicotinic acid, 26.6µM glycine, 1.7 mM myo-inositol, 3.43 mM L-glutamine, 3.25 mM L-glutathione reduced, 10 mg/L AG Larcoll™, 100 mg/L cefotaxime, 90 g/L maltose, 9 g/L mannitol, 0.2 mg/L 2,4-dichlorophenoxyacetic acid, 1 mg/L phenylacetic acid and 0.2 mg/L kinetin, adjusted to pH 7.0 with KOH) in a 15 mL tube and pelleted again at 100×g for 5 minutes at 4° C. The pellet was then re-suspended in 15 mL CIMC wash supplemented with SS-31 peptide (CanPeptide Inc. Canada; D-Arg-Dmt-Lys-Phe-$NH_2$; final concentration: 6.6 mg/mL) and pelleted as before. The pellet was re-suspended again in 7 mL 20% (w/v) maltose solution and 1 mL of CIMC wash was layered on top in a 15 mL Falcon™ tube, and centrifuged at 100×g for 13 minutes at 4° C. A band of viable microspores at the interface of the CIMC wash and maltose was removed with a 1 mL pipette, and then cells were re-suspended in 15 mL CIMC wash and pelleted at 150×g for 5 minutes at 4° C. The supernatant was decanted leaving an approximately 400µL pellet of microspores at the bottom of the Falcon tube. These cells were re-suspended with 1 mL of CIMC wash and subsequently quantified using a haemocytometer. Finally, the microspore suspension was diluted with CIMC wash to the final concentration 500 cells/µL.

DNA Preparation

DNA containing the first nif operon (nifHDKY) was produced by restriction enzyme digest of the pOA_nifclusterfrag1 plasmid DNA with SfiI and AscI enzymes (NEB), followed by extraction of a 5.3 kb long DNA from agarose gel and purification using NucleoSpin™ Gel and PCR Clean-up kit (Macherey-Nagel) according to the supplier manual. Alternatively, the 5.3 kb DNA was generated by PCR in a 25µL reaction containing Phusion™-HF buffer, 0.2 mM dNTPs, 0.5µM of each primer (AZ114 (CA-CATGGGTCTGGTCAGGAA (SEQ ID NO: 6); forward primer) and AZ115 (CGAGGACCTTTATAGCCATAAT-TCA (SEQ ID NO: 7); reverse primer)), 50 pg plasmid DNA and 0.25µL Phusion™-HF enzyme (Life Technologies). Cycling was performed as follows: at 98° C. for 30 sec, 30 cycles of 98° C. for 10 sec, 60° C. for 30 sec, 72° C. for 3 min, and 72° C. for 10 min. The PCR product was purified using NucleoSpin™ Gel and PCR Clean-up kit (Macherey-Nagel).

Microspore Transfection

DNA (1.5µg) was combined with each of the five mitochondrial targeting nanocarrier polypeptides (mTPs) listed in Example 1 at various weight-to-weight (w/w) peptide:DNA ratios in a final volume of 100µl Optima™ $dH_2O$ (Fisher Scientific). The mixture was incubated for 15 min at room temperature to form nanocomplexes between the mTP and the DNA, and then incubated with isolated triticale microspores (200µL, 1×$10^5$ cells) for 15 min at room temperature. CIMC wash (500µL) was added, and the mixture was incubated for 45 min at room temperature. Next, microspores were pelleted by centrifugation at 100×g for 5 minutes at room temperature, 600µL of the supernatant were removed and microspores were re-suspended in the remaining 200µL. The transformation mixture was then added to 3.5 cm Petri dishes containing 3.3 ml CIMC wash supplemented with PSK-α peptide (CanPeptide Inc. Canada; Tyr (4-$OSO_3H$)-Ile-Tyr(4$OSO_3H$)-Thr-Gln; final concentration: 85 ng/mL) for transient experiments or 3.3 ml CIMC-7 medium (a microspore culture and embryo induction medium composed of CIMC wash supplemented with Ficoll™ (final concentration: 10% (w/v))) with PSK-α peptide and four ovaries for embryogenesis and selection experiments. Microspores were cultivated at 28° C. in the dark. The control cultures were carried out on microspores treated in the absence of transfecting peptide or DNA (negative transfection controls).

RNA Extraction from the Transfected Microspores

Microspores from four transfections were pooled and harvested by centrifugation: first in a 15 mL Falcon™ tube at 4000 rpm for 5 min at room temperature and then in a 2 mL grinding tube at 10,000 rpm for 1 minute. The supernatant was removed, 6 stainless steel beads (2.38 mm width; MO BIO Laboratories Inc.) were added, and the cells were immediately frozen in liquid nitrogen and stored at −80° C.

Total RNA was extracted using Plant RNeasy™ Kit (Qiagen) according to the manufacturer's instructions, with few modifications. Cells were thawed by re-suspension in 450μL RLT/βME buffer and cell lysis was done by vortexing the horizontally placed tubes in a Vortex-Genie™ 2 mixer (Fisher Scientific) for 15 min at maximum speed, at room temperature. In addition, two DNase treatments were included: on column and in a tube, the latter followed by RNA clean-up according to the manufacture's protocol. Each DNase treatment was done for 30 min at 37° C. in 100μL reaction containing 10 U of Turbo™ DNaseI (Fisher Scientific). Purified RNA was quantified using UV-vis spectroscopy on a Nanodrop™ 8000 instrument (ThermoFisher Scientific).

qRT-PCR Analysis cDNA was synthesized using a Superscript™ VILO cDNA synthesis kit (Life Technologies) according to the manufacturer's instructions with a total of 400 ng of RNA template per 20μL reaction. All real time PCR reactions were performed using QuantiTect™ SYBR™ Green PCR Master Mix (Qiagen) in a 20μl reaction volume. Each sample was tested in triplicate, and 2μl (40 ng) of template were used for each reaction along with 0.1μM of each forward and reverse primer (Table 1). Cycling was performed as follows: at 95° C. for 15 min, 40 cycles of 95° C. for 15 sec, 60° C. for 30 sec, 72° C. for 30 sec, followed by a dissociation curve. Relative expression of the nif genes was calculated in relation to the expression of the mitochondrial endogenous cob (cytochrome b), coxII (cytochrome c oxidase subunit II) and rpS13 (ribosomal protein S13) genes, using the standard curve method or relative standard curve method with fresh non-transfected microspores serving as a reference sample for analysis with QuantStudio™ software. Relative expression of the daao gene was calculated in relation to the expression of the mitochondrial endogenous cob gene, using the standard curve method.

TABLE 1

Primer sequences

| Target | Primer name | Forward/ Reverse | Sequence | Sequence identifier |
|---|---|---|---|---|
| nifHDKY operon | AZ114 | F | CACATGGGTCTGGTCAGGAA | SEQ ID NO: 6 |
| | AZ115 | R | CGAGGACCTTTATAGCCATAATTCA | SEQ ID NO: 7 |
| nifH | AZ076 | F | CTGCTGAAGTGGGATCCGTT | SEQ ID NO: 8 |
| | AZ077 | R | CTCGTCCAGCACATCCAACA | SEQ ID NO: 9 |
| nifD | AZ078 | F | TGACTGTTCGTGGATGTGCT | SEQ ID NO: 10 |
| | AZ079 | R | CCACACCAGAAACACCGGTA | SEQ ID NO: 11 |
| nifK | AZ084 | F | TGCTTGGACTACTACCGCTG | SEQ ID NO: 12 |
| | AZ085 | R | GCAACACATCCTTGGGATCC | SEQ ID NO: 13 |
| nifY | AZ173 | F | TGCTTGGACTACTACCGCTG | SEQ ID NO: 14 |
| | AZ174 | R | GCAACACATCCTTGGGATCC | SEQ ID NO: 15 |
| nifB | AZ201 | F | ATCATGCAGCCAGAACAGCT | SEQ ID NO: 16 |
| | AZ202 | R | ACAAGCTGGAGCAACAGGAA | SEQ ID NO: 17 |
| nifQ | AZ203 | F | CTCCTCGAGATTGGCAAGCT | SEQ ID NO: 18 |
| | AZ204 | R | AGGTCCAGCATCTTGTTGCA | SEQ ID NO: 19 |
| nifE | AZ205 | F | ACCCGATATCATCCTGCTGC | SEQ ID NO: 20 |
| | AZ206 | R | ATCACATCACCAGCAGGACG | SEQ ID NO: 21 |
| nifN | AZ207 | F | CCTGCTGATCTTTTGGTGGC | SEQ ID NO: 22 |
| | AZ208 | R | TCCTTGACGAACACGACGAA | SEQ ID NO: 23 |
| nifF | AZ209 | F | TCTGCTCGTGGTGCTCAAAT | SEQ ID NO: 24 |
| | AZ210 | R | AGCCAAGAAGCAAGACGAGC | SEQ ID NO: 25 |
| nifJ | AZ211 | F | TGGAACTGCTGCTTGGGAAA | SEQ ID NO: 26 |
| | AZ212 | R | AGAGCAGGACGAATAGCAGC | SEQ ID NO: 27 |
| nifU | AZ213 | F | CTCCTGCTGTTGCTTCTGGA | SEQ ID NO: 28 |
| | AZ214 | R | CCAGACAAAGACACGGTCACT | SEQ ID NO: 29 |
| nifS | AZ215 | F | GGGTGCTGCTTGTGAATTGG | SEQ ID NO: 30 |
| | AZ216 | R | CAGGAACAGCAGGTTGTCCA | SEQ ID NO: 31 |
| nifV | AZ217 | F | AGGATTGGGAGAACGTGCTG | SEQ ID NO: 32 |
| | AZ218 | R | GCCACACGTTGACAAGAAGC | SEQ ID NO: 33 |

TABLE 1-continued

Primer sequences

| Target | Primer name | Forward/ Reverse | Sequence | Sequence identifier |
| --- | --- | --- | --- | --- |
| nifW | AZ219 | F | TGATGAACTTCGATCCGCTGA | SEQ ID NO: 34 |
|  | AZ220 | R | AAGAGGCACTTCAGCACGAA | SEQ ID NO: 35 |
| nitZ | AZ221 | F | TCAACCATGGCTTGCTGGAA | SEQ ID NO: 36 |
|  | AZ222 | R | ACAGAAAACCAACGACCGGA | SEQ ID NO: 37 |
| nifM | AZ223 | F | GCTCGTGTTCCTGAAGGTGA | SEQ ID NO: 38 |
|  | AZ224 | R | CTGGTTGAGGAGCTTGTCGA | SEQ ID NO: 39 |
| cob | 336F | F | AGAATGGCATGGATCGGTAG | SEQ ID NO: 40 |
|  | 440R | R | TCCTAATGTTTTGGGCATC | SEQ ID NO: 41 |
| coxll | 95F | F | TTCCACGAATCTCACTGCAC | SEQ ID NO: 42 |
|  | 241R | R | GTTGGGCTGTACCTTCCTCA | SEQ ID NO: 43 |
| rpS13 | 64F | F | GTAAGGGCGATCCATCTTGA | SEQ ID NO: 44 |
|  | 156R | R | GGGAATTGAAGAGGGGAGAA | SEQ ID NO: 45 |
| daao | AZ197 | F | GAATTGTTCCACGGCAAGGG | SEQ ID NO: 46 |
|  | AZ198 | R | CAGCTTGGTATCCTGTGCCA | SEQ ID NO: 47 |

Transient Expression of the nifHDKY Genes

Figure 4:
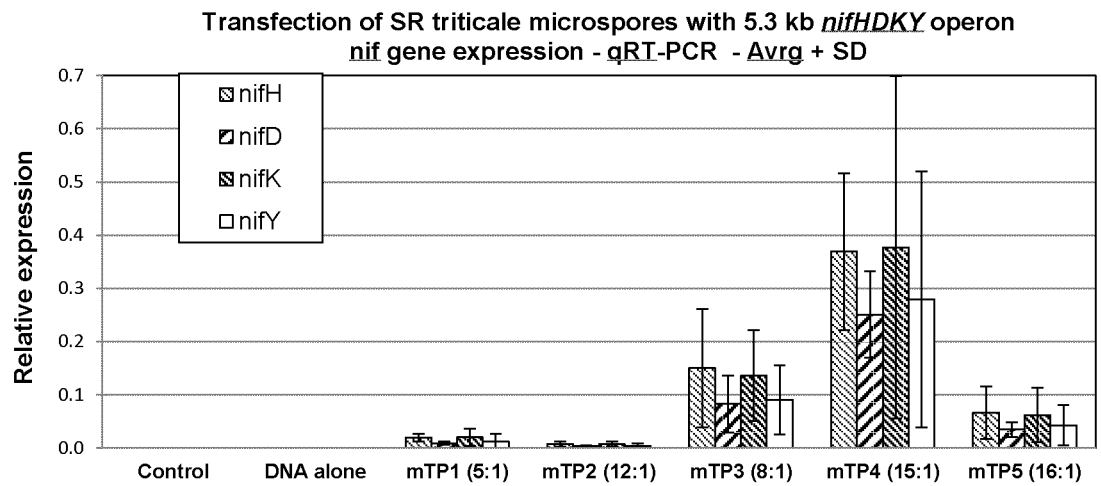
FIG. 4 is a graph showing the relative level of expression of the nifHDKY operon in triticale microspores transfected with nanocomplexes formed from various combinations of mTPs and nifHDKY DNA.

The nif operon 1 DNA (nifHDKY) was delivered as a nanocomplex between the DNA (1.5µg) and mTPs. A low peptide:DNA ratio was chosen to formulate the nanocomplexes, based on the results of the DNA binding and DNase protection assays: specifically, a 5:1 w/w mTP1 peptide:DNA ratio (mTP1 (5:1)), a 12:1 w/w mTP2 peptide:DNA ratio (mTP2 (12:1)), an 8:1 w/w mTP3 peptide:DNA ratio (mTP3 (8:1)), a 15:1 w/w mTP4 peptide:DNA ratio (mTP4 (15:1)) and a 16:1 w/w mTP5 peptide:DNA ratio (mTP5 (16:1)), as indicated in FIG. 4. The nif transcript abundance in triticale microspores 48 h after transfection was analyzed by qRT-PCR. Three repetitions were used to measure the fold difference of normalized nif mRNA expression compared to the control levels of mitochondrial endogenous mRNA expression of cob, coxII and rpS13 genes, using a standard curve method.

As seen from the results shown in FIG. 4, qRT-PCR analysis on total RNA isolated from the transfected microspores showed that all four nif gene transcripts could be detected 48 hours post transfection, while no nif transcript was detected in control microspores. Interestingly, it was observed that mTP4 was the best carrier for the nifHDKY operon at a low peptide:DNA ratio, followed by mTP3 and mTP5, whereas expression of the nif genes delivered by mTP1 and mTP2 peptides at a low peptide:DNA ratio was very low.

Optimization of Delivery of the nifHDKY Genes into Triticale Microspores

Figure 5A:
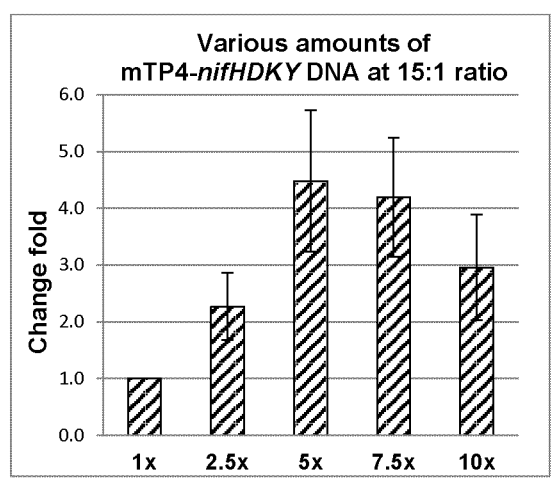
FIG. 5A is a graph showing transient expression of the nifHDKY operon in triticale microspores transfected with various amounts of nanocomplexes formed from mTP4 and nifHDKY DNA at a peptide:DNA ratio of 15:1 (w/w)

As shown in FIG. 4, it was observed that the average nif gene expression was generally low: ~30% of the reference gene expression (endogenous mitochondrial genes) for mTP4-mediated delivery, which may be too low to allow detection of the Nif proteins. Therefore, two strategies to increase nif gene delivery and expression were tested: (i) use of a higher peptide:DNA ratio and (ii) delivery of higher amounts of the nanocomplex formed at low peptide:DNA ratio. Thus, triticale microspores were incubated as described above with mixtures of mTP4 and increasing amounts of the nif operon 1 DNA (obtained from Fragment 1 shown in FIG. 3B as described above) at a 15:1 w/w peptide:DNA ratio; specifically nanocomplexes formed from 1.5µg of DNA (1×), 3.75µg of DNA (2.5×), 7.5µg of DNA (5×), 11.25µg of DNA (7.5×) and 15µg of DNA (10×). The results are shown in FIG. 5A. In addition, in a separate experiment, triticale microspores were incubated as described above with nanocomplexes formed from each of mTP1, mTP2, mTP3, mTP4 and mTP5 with 1.5µg of the nif operon 1 DNA (obtained from Fragment 1 shown in FIG. 3B as described above) at a peptide:DNA ratio of 100:1 w/w. The results are shown in FIG. 5B.

Figure 5B:
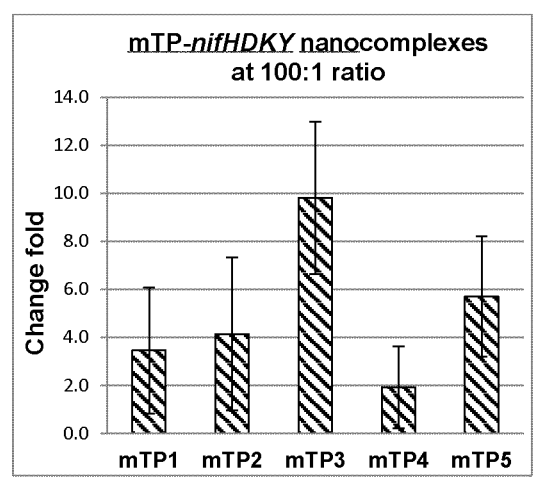
FIG. 5B is a graph showing transient expression of the nifHDKY operon in triticale microspores transfected with standard amounts of nanocomplexes formed from various combinations of mTPs and nifHDKY DNA at a peptide:DNA ratio of 100:1 (w/w)

As can be seen from the results shown in FIGS. 5A and 5B, both strategies resulted in a significant increase in the nif gene expression, with the best results obtained for mTP3 at a 100:1 w/w peptide:DNA ratio with a standard nanocomplex amount (based on 1.5µg of DNA) (FIG. 5B; mTP3_100_1×) and mTP4 at 15:1 w/w peptide:DNA ratio combined with a 5-fold higher amount of the nanocomplex (based on 7.5µg of DNA) (FIG. 5A; mTP4_15_5×).

Example 3

Production of Nif Proteins in Transfected Triticale Microspores

In order to detect production of the Nif proteins in transfected cells, protocols were developed for isolation of total protein extract from triticale microspores and for detection of the mitochondrial proteins in these extracts. Anti-NifH antibody was used to detect the NifH protein resulting from the expression of the delivered nifHDKY operon, whereas anti-Idh and anti-CoxII antibodies were applied to detect the mitochondrial endogenous proteins Idh (isocitrate dehydrogenase) and CoxII (cytochrome oxidase subunit II), which served as controls of the protein extract quality.

Total Protein Extraction

Microspores were transfected as described in Example 2. Total protein was extracted from microspores 0, 1, 2, 3, 4, 5 and 7 days post transfection by sonication in the Protein Solubilisation Buffer (Cedarlane), according to the manufacturer's instructions. Protein concentration in the extracts was determined using DC™ Protein Assay (BioRad).

Western Blotting

Ten μg of the total protein extract were separated in two parallel SDS-PAGE electrophoresis gels (Laemmli UK, Nature (1970), 227: 680-685) using Bolt™ 12% Bis-Tris Plus Gels and Bolt™ MES SDS Running Buffer (Life Technologies), and then electrotransferred onto a polyvinylene difluoride (PVDF) (0.2μm) membrane (Millipore) as described previously (Towbin et al., Proc. Natl. Acad. Sci. USA (1979), 76: 4350-4354) using Bolt™ Transfer Buffer (Life Technologies). After the transfer was completed, the membrane was washed three times for 5 min in 1×PBS (phosphate-buffered saline, BioShop) supplemented with 0.5% (v/v) Tween 20 (PBS-T) and blocked with PBS-T containing 5% fat-free milk (PBS-TB; BioShop) for 30 min. The membrane was incubated overnight at 4° C. with primary antibody: hen polyclonal anti-NifH IgY antibody, rabbit polyclonal anti-CoxII or anti-Idh IgG antibody (Agrisera; dilution 1:1,000). After repeated washing in PBS-TB, the membrane was incubated for 2 h at room temperature with goat anti-chicken IgY or goat anti-rabbit IgG HRP-conjugate (Agrisera, dilution 1:5,000). After several washes in PBS-T, immunodetection was performed using Bolt™ TMB-Blotting Substrate Solution (Thermo Scientific) at room temperature. Lanes with a visible band corresponding to NifH protein were marked on wet membranes. Images of dried membranes were then taken in BioRad Gel Doc XR+ Imaging System using the Image Lab software (program: Blot/Colorimetric/Image color: Grey).

Figure 6:
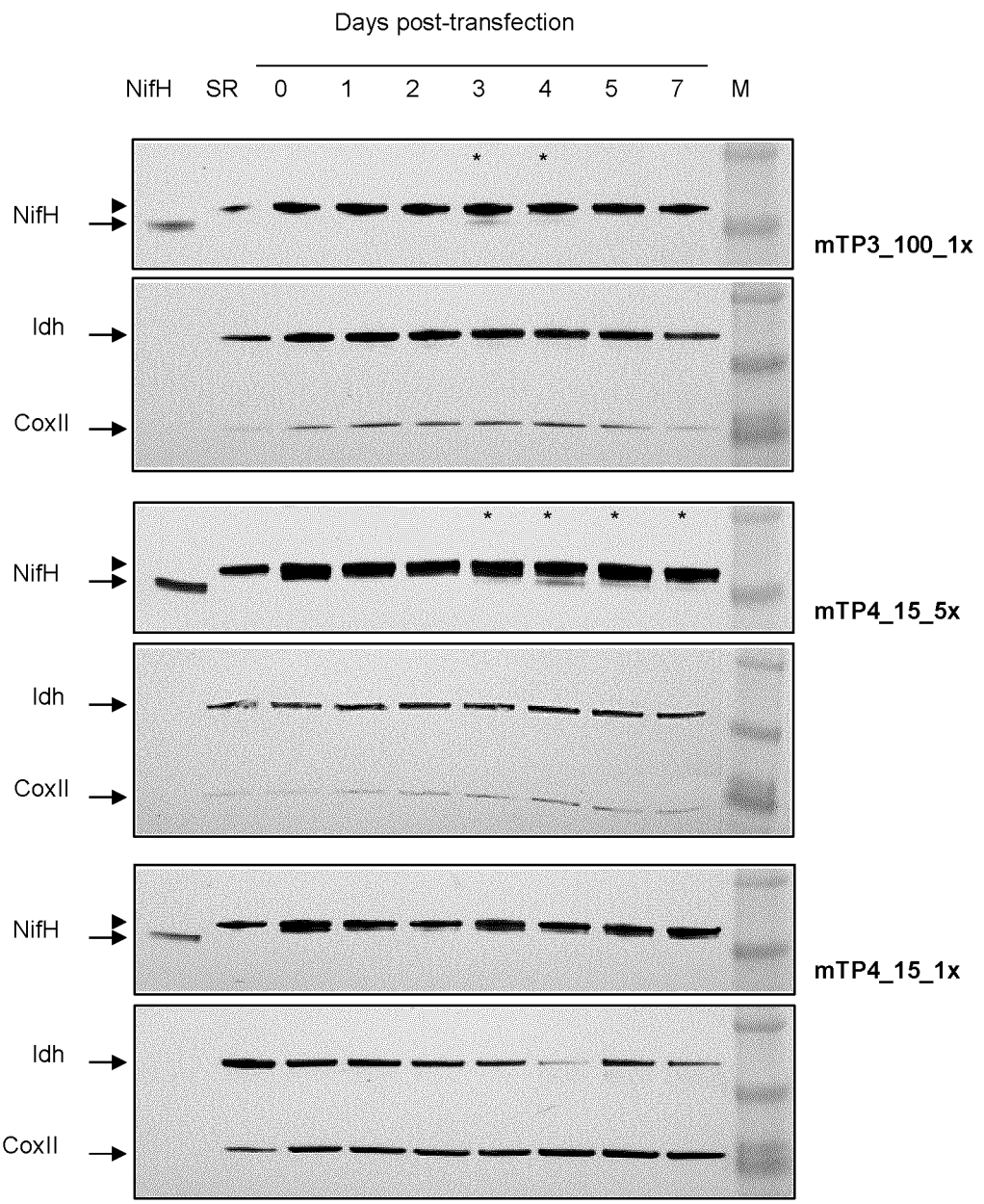
FIG. 6 is a series of photographs showing a Western blot analysis of total protein extracts isolated from triticale microspores transfected with mTP-nifHDKY nanocomplexes. Lanes containing the NifH protein on wet blots are indicated with *. Arrowhead (▸) indicates an unknown NifH-like protein. Idh and CoxII indicate the mitochondrial endogenous proteins isocitrate dehydrogenase and cytochrome oxidase subunit II, respectively. Lane NifH is a recombinant NifH protein control. Lane SR is total protein extract from untreated triticale (cv. Sunray) microspores. Lane M is a protein size marker (SeeBlue™ Plus2)

As seen from the results presented in FIG. 6, Western blot analysis of the transfected microspores showed the presence of low but detectable amounts of the NifH protein 3-7 days post transfection in the extracts isolated from microspores transfected with nanocomplexes formed with the nifHDKY operon DNA and mTPs: mTP3_100_1× and mTP4_15_5× but not mTP4_15_1×. These results demonstrated that the nifHDKY operon was functional in triticale microspore mitochondria and the nif genes were expressed not only at the transcript level but also at the protein level.

Example 4

Delivery of the nif Cluster into Triticale Microspores

The nif cluster DNA fragments 1, 2 and 3 shown in FIG. 3B were prepared by excision from the pOA_nifclusterfrag1, pMK-V-Bs_nifclusterfrag2 and pMK-RQ_nifclusterfrag3 plasmid vectors, respectively (described in Example 2), with SfiI restriction enzyme, followed by separation in 0.8% agarose and purification using NucleoSpin™ Gel and PCR Clean-up kit (Macherey-Nagel) according to the supplier manual and nanocomplexes were prepared.

Each of the nif cluster fragments 1, 2 and 3 was incubated separately (S) for 15 minutes at room temperature with mTP4 at a 15:1 (w/w) peptide:DNA ratio using a standard (1.5μg) amount of each DNA fragment in an individual 75μL reaction volume. The three individual nanocomplex mixtures (one for each of Fragments 1, 2 and 3) were then combined (4.5μg total DNA; total volume 225μL) to provide the nanocomplex mTP4_Nif1,2,3(S)_15_1×. Similarly, each of the nif cluster fragments 1, 2 and 3 was incubated separately (S) with mTP4 at a 15:1 (w/w) peptide:DNA ratio using a five-times higher amount (7.5μg) of each DNA fragment, and the individual mixtures were combined (22.5μg total DNA; total volume 225μL) to provide the nanocomplex mTP4_Nif1,2,3(S)_15_5×. Finally, each of the nif cluster fragments 1, 2 and 3 was incubated separately (S) with mTP3 at a 100:1 peptide:DNA ratio using a standard amount (1.5μg) of DNA, and the individual mixtures were combined (4.5μg total DNA; total volume 225μL) to provide the nanocomplex mTP3_Nif1,2,3(S)_100_1×.

Additionally, the appropriate mTP (mTP4 or mTP3) was incubated with pooled (P) DNA fragments (Fragments 1, 2 and 3) in a total volume of 200μL for 15 minutes at room temperature to prepare pooled nanocomplexes. Thus, reaction of mTP4 at a 15:1 (w/w) peptide:DNA ratio using a standard (1.5μg) amount of each of DNA fragments 1, 2 and 3 (4.5μg total DNA) provided the pooled nanocomplex mTP4_Nif1,2,3(P)_15_1×; reaction of mTP4 at a 15:1 (w/w) peptide:DNA ratio using a 5× (7.5μg) amount of each of DNA fragments 1, 2 and 3 (22.5μg total DNA) provided the pooled nanocomplex mTP4_Nif1,2,3(P)_15_5×; and reaction of mTP3 at a 100:1 (w/w) peptide:DNA ratio using a standard amount (1.5μg) of each of DNA fragments 1, 2 and 3 (4.5μg total DNA) provided the pooled nanocomplex mTP3_Nif1,2,3(P)_100_1×.

Microspores were transfected with the nanocomplexes using the method described in Example 2. The relative abundance of transcripts of the first nif gene in each fragment was measured by qRT-PCR as described in Example 2 at 48 hours after transfection. Three repetitions were used to measure the fold difference of normalized nif mRNA expression compared to the control levels of mitochondrial endogenous mRNA expression (cob gene) using the relative standard curve method (QuantStudio™ software) and fresh non-transfected microspores as reference sample.

Figure 7A:
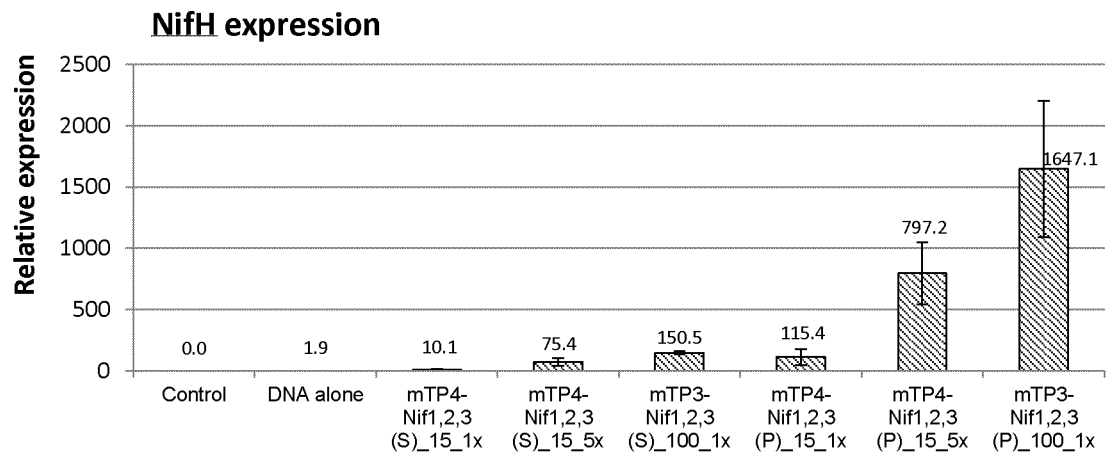
FIG. 7A is a bar graph showing transient expression of the nifH gene of the nif cluster fragment 1 of FIG. 3B in triticale microspores transfected with various nanocomplexes formed by mixing mTP3 or mTP4 at various ratios and amounts with each of nif cluster fragments 1, 2 and 3 separately (S) or pooled (P)
Figure 7B:
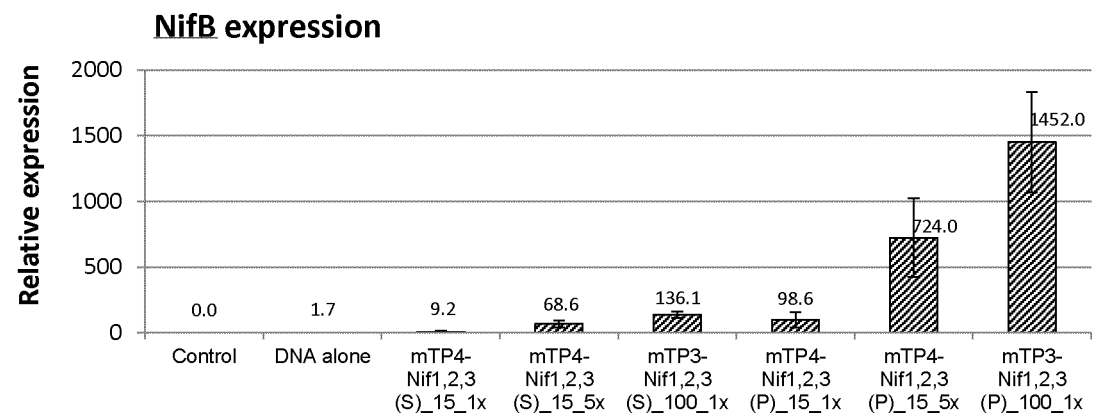
FIG. 7B is a bar graph showing transient expression of the nifB gene of the nif cluster fragment 2 of FIG. 3B in triticale microspores transfected with the nanocomplexes of FIG. 7A.
Figure 7C:
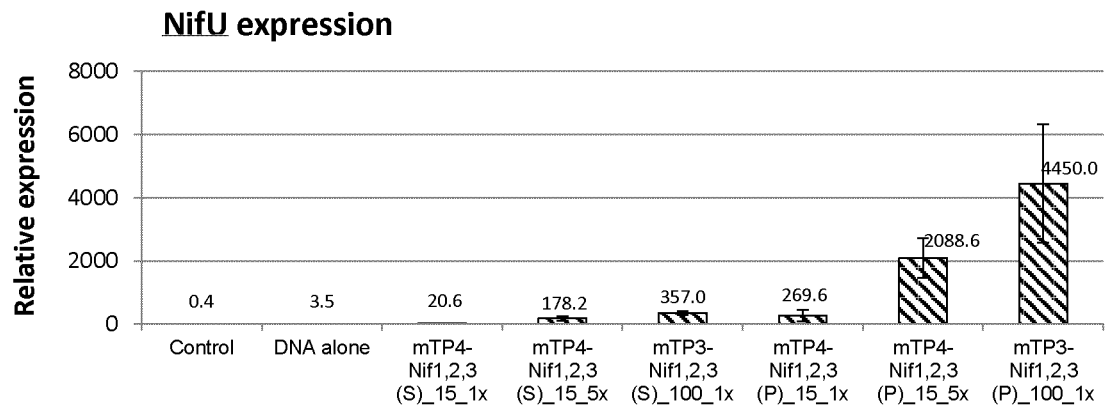
FIG. 7C is a bar graph showing transient expression of the nifU gene of the nif cluster fragment 3 of FIG. 3B in triticale microspores transfected with the nanocomplexes of FIG. 7A.

As seen from the results presented in FIGS. 7A to C, all three nif transcripts: nifH (Fragment 1), nifB (Fragment 2) and nifU (Fragment 3) were detected in the transfected microspores but not in the control microspores, thus confirming that all three nif cluster fragments were delivered into triticale microspores. Expression of the nifH, nifB and nifU genes was highest in microspores transfected with mTP3_100_1× nanocomplexes, moderate in microspores transfected with mTP4_15_5× nanocomplexes and low in microspores transfected with mTP4_15_1× nanocomplexes. Interestingly, nif genes delivered as mTP-pooled (P) DNA nanocomplexes are expressed more efficiently than those delivered as mTP-separate (S) DNA nanocomplexes.

Figure 8:
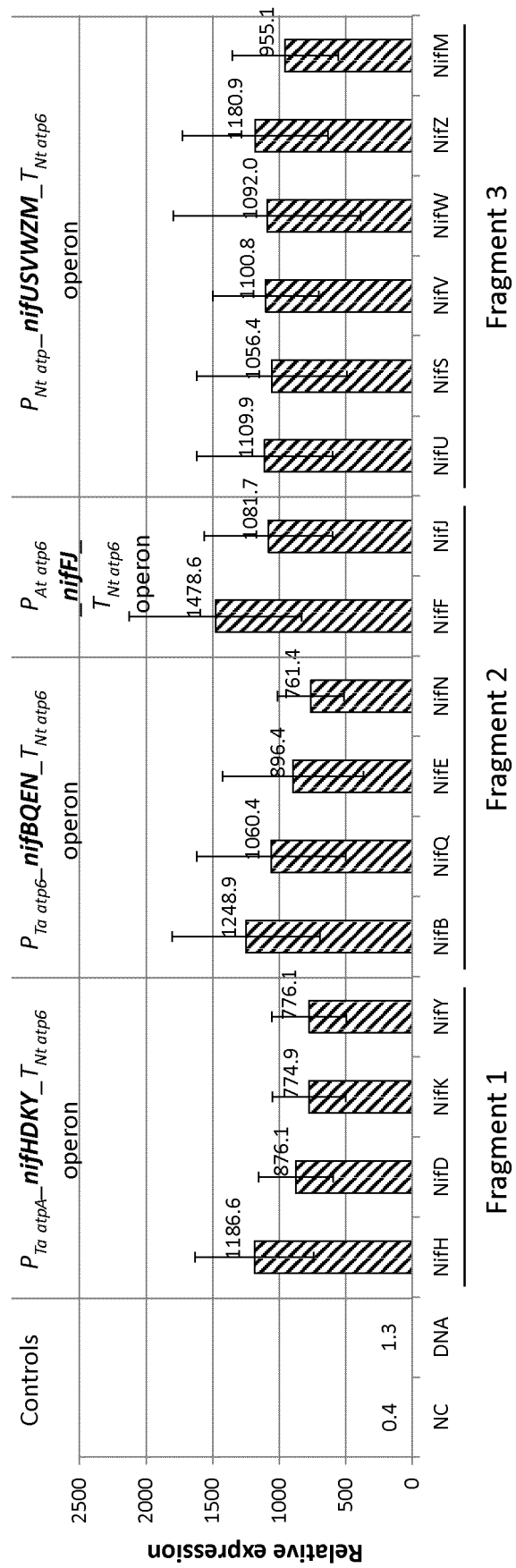
FIG. 8 is a bar graph showing transient expression of the nif cluster genes in triticale microspores transfected with the nanocomplex mTP4_Nif1,2,3(P)_15_5x of FIG. 7A.

Expression of all four nif operons (nifHDKY, nifBQEN, nifFJ and nifUSVWZM) of the three fragments of the nif cluster delivered as mTP-pooled DNA nanocomplexes was tested. As seen from the results presented in FIG. 8 for the pooled nanocomplex mTP4_Nif1,2,3(P)_15_5×, qRT-PCR analysis revealed that all 16 nif transcripts of the nif cluster (Fragments 1, 2 and 3) were detected, thus confirming that all nif genes delivered into triticale microspores were expressed. The expression levels for various nif genes were noticed to be diverse, most likely due to differences in promoter strength and transcript stability.

Example 5

Nitrogen Fixation in Transiently Transfected Microspores $N_2$ Fixation Assay

To test the ability of the nif-transfected triticale microspores to fix atmospheric nitrogen ($N_2$), a protocol for the $^{15}N_2$ incorporation assay that has been developed for bacterial cells (Temme et al., Proc. Natl. Acad. Sci. USA (2012), 109: 7085-7090) was adapted for microspores. As a positive control, anaerobic cultures of Klebsiella oxytoca strain M5a1 cultivated in a de-repression medium in the presence of 98 atom percent (AT %) and 9.8AT % $^{15}N_2$ gas were used. Microspores were isolated as described in Example 2, using a repression medium (CIMC wash deprived of inorganic and organic nitrogen source, i.e. without $(NH_4)_2SO_4$, glutamine and glutathione) instead of standard CIMC wash, and then transfected with pooled mTP_Nif1,2,3 DNA nanocomplexes formed as described in Example 4 by reacting nif cluster fragments 1, 2 and 3 with mTP4 at a 15:1 (w/w) peptide:DNA ratio using standard (T4_Nif_15_1) or five-times higher amounts of DNA (T4_Nif_15_5), or with mTP3 at a 100:1 (w/w) peptide:DNA ratio using a standard amount of DNA (T3_Nif_100_1). Next, 3.0 ml de-repression medium (repression medium supplemented with D-serine, as described previously for *Klebsiella* (Temme et al., Proc. Natl. Acad. Sci. USA (2012), 109: 7085-7090)) in 12.0 ml glass tubes with an open plastic cap containing a rubber seal disc (Isomass Scientific Inc., #E2850-5) were inoculated with control and transfected microspores (250μL, 1×10⁵ cells). The headspace (9 ml) of the tubes was replaced by $^{15}N_2$ labelled air by injecting compressed $^{15}N_2$ labelled air through the rubber seal of the tube with simultaneous evacuation of the unlabeled (natural) air through a vent needle. Compressed $^{15}N_2$ labelled air was generated by mixing $^{15}N_2$ (98AT %; Sigma) gas and $O_2$ at 80:20 (v:v) ratio in 150 mL glass tubes (hermetically sealed with a rubber disc and metal cap) containing 1 g of oxalic acid to eliminate inorganic N contaminants, after evacuation of the air by vacuum and flushing the tubes with natural $N_2$ gas. In parallel, natural air was used instead of $^{15}N_2$ labelled air. Control and nif-transfected cells were cultured for 7 days at 28° C. in the dark, and then harvested by centrifugation at 150×g for 5 min. at room temperature, and the cell pellets were dried in a laboratory oven at 60° C. for 24 h. The dried cell samples were analysed for nitrogen content and $^{15}N$ to total N ratio (AT %) by using the Finnigan MAT Deltaplus™ Isotope Ratio Mass Spectrometer.

Figure 9A:
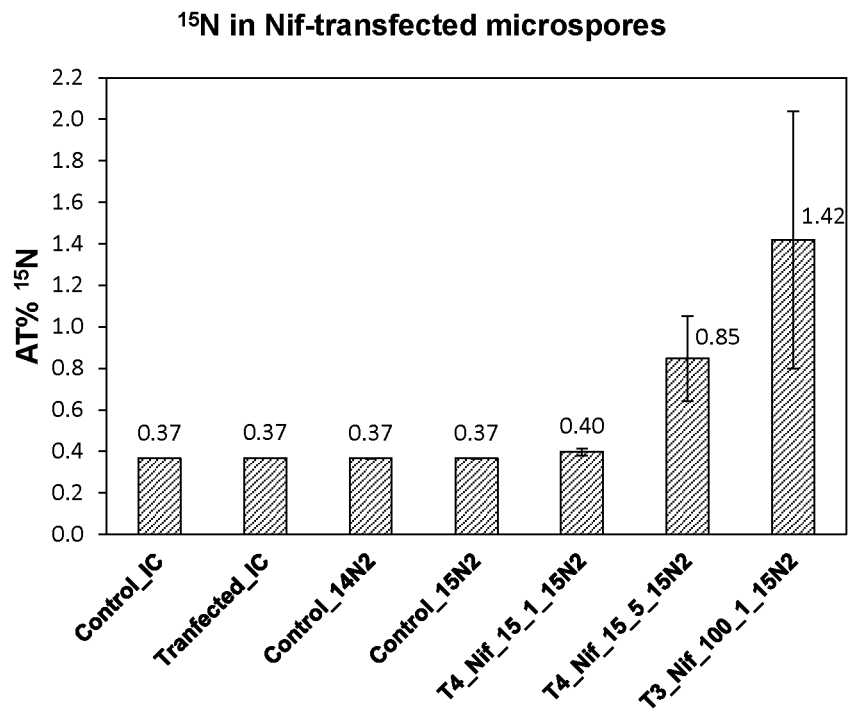
FIG. 9A is a bar graph showing the atom percent (AT %) of $^{15}N$ incorporated into control triticale microspores and triticale microspores transfected with nif genes. IC indicates initial culture.
Figure 9B:
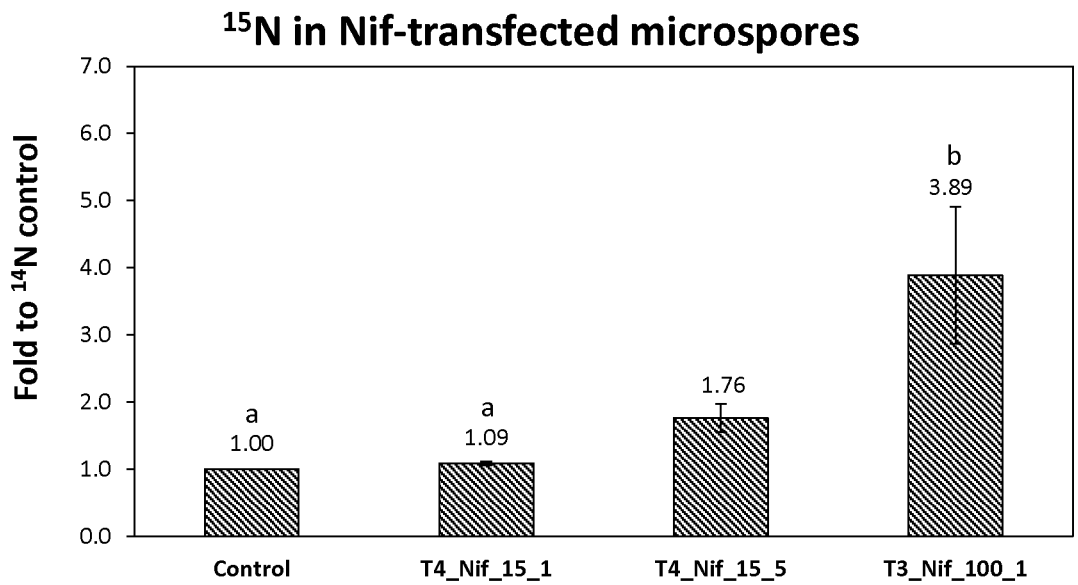
FIG. 9B is a bar graph showing the fold difference in $^{15}N$ content versus $^{14}N$ control for the transfected triticale microspores of FIG. 9A. Pairwise statistical analysis using ANOVA with Tukey test showed significant difference for treatments indicated as "b", with significance of $p<0.05$, and no significance for treatments indicated as "a"

As seen from the results presented in FIGS. 9A and 9B, $^{15}N$ content in the initial cultures of control and transfected microspores as well as in control microspores cultured in the natural and labelled air was the same and corresponded to the natural abundance of $^{15}N$ isotope (0.366 AT %), as expected. This confirmed that non-transfected microspores did not have the ability to fix atmospheric nitrogen. Detectable enrichment in the $^{15}N$ content was detected in nif-transfected microspores. $^{15}N$ amount in dry cell biomass was increased by 10% in microspores transfected with the T4_Nif_15_1 nanocomplexes, whereas in cells transfected with T4_Nif_15_5 and T3_Nif_100_1 nanocomplexes the increase was 2.1 and 3.6 fold, respectively. This increase in the $^{15}N$ content in transfected microspores indicates that nif gene cluster delivery resulted in functional expression of nif genes in the mitochondria of Nif-positive microspores, leading to incorporation of atmospheric nitrogen into the cell biomass (nitrogen fixation).

Example 6

Selection Marker Genes

Cell Viability Test—FDA Assay

A sample of isolated triticale microspores (10,000-20,000 cells) re-suspended in 270μL CIMC wash was mixed with 60μl of FDA (fluorescein diacetate, 100 ng/ml solution in CIMC wash), and incubated for 5 minutes in the dark. Green fluorescent (viable) and non-fluorescent (dead) cells were observed and counted using a Leica EVOS™ fluorescence microscope (total count per sample: 100 cells).

Microspore Embryogenesis and Embryo Germination

Microspores (1×10⁵ cells per plate) were cultured in 3.5 mL CIMC-7 medium with or without various concentrations of the selection agents D-alanine (D-Ala, Sigma) and/or streptomycin (Strep; Sigma) in the dark at 28° C. At 4 weeks, the developing embryos were transferred onto solid CIMC-4 medium (13.4 mM $KNO_3$, 1.8 mM $(NH_4)_2SO_4$, 1.5 mM $KH_2PO_4$, 0.56 mM $CaCl_2$, 0.38 mM $MgSO_4$, 2.4μM KI, 29.6μM $MnSO_4$, 80.9μM $H_3BO_3$, 17.4μM $ZnSO_4$, 52.5 nM $CoCl_2$, 50 nM $CuSO_4$, 52 nM $Na_2MoO_4$, 0.1 mM $FeSO_4$, 0.1 mM $Na_2EDTA$, 89.6μM MES hydrate, 29.7μM thiamine, 142μM ascorbic acid, 4.86μM pyridoxine, 8.12μM nicotinic acid, 75μM L-aspartic acid, 52μM citric acid, 26.6μM glycine, 1.7 mM myo-inositol, 3.43 mM L-glutamine, 4.3μM L-proline, 100 mg/L cefotaxime, 1 mg/L spermine, 4 mg/L spermidine, 60 g/L maltose, 9 g/L mannitol, 1 mg/L phenylacetic acid, 2 mg/L 6-Benzylaminopurine, 0.5 mg/L metatopoline and 3 g/L [0.3% (w/v)] Gelrite™, adjusted to pH 5.8 with KOH) containing various concentrations of the selection agents D-alanine and/or streptomycin, and cultured at 16° C. beneath Sylvania Gro-lux™ wide spectrum bulbs (40 watts) delivering 80μM m$^{-2}$ s$^{-1}$ (a 16-h light period). Germinating embryos were scored after 3-4 weeks of culture. Plant regeneration efficiency was defined as the number of green plantlets germinated from 100 embryos, expressed as a percentage.

DAAO Selection

Figure 10A:
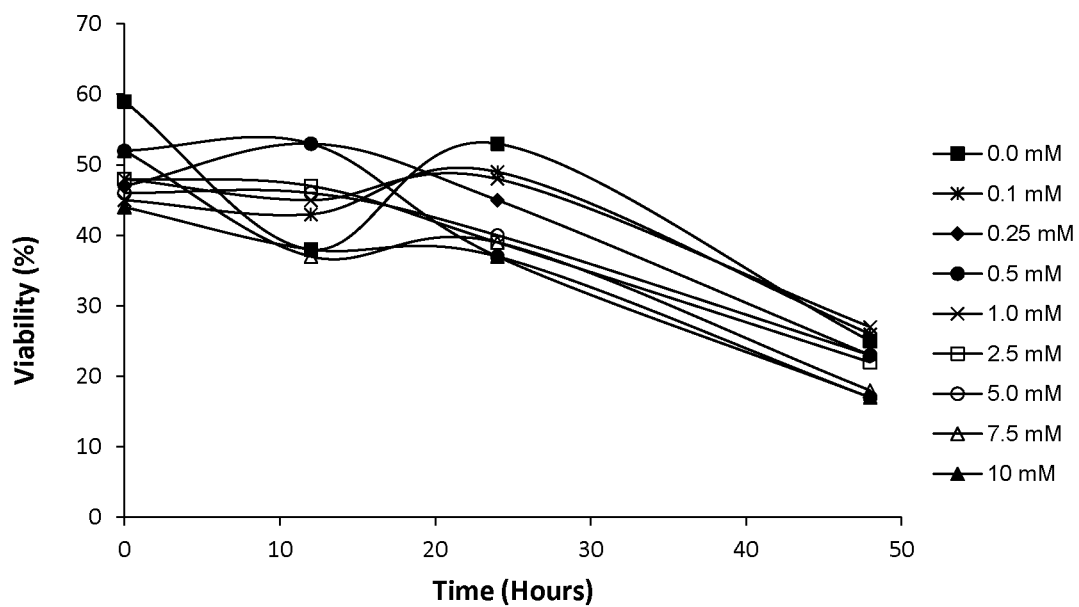
FIG. 10A is a graph showing the viability of triticale microspores over time in the presence of various concentrations of D-alanine (D-Ala)
Figure 10B:
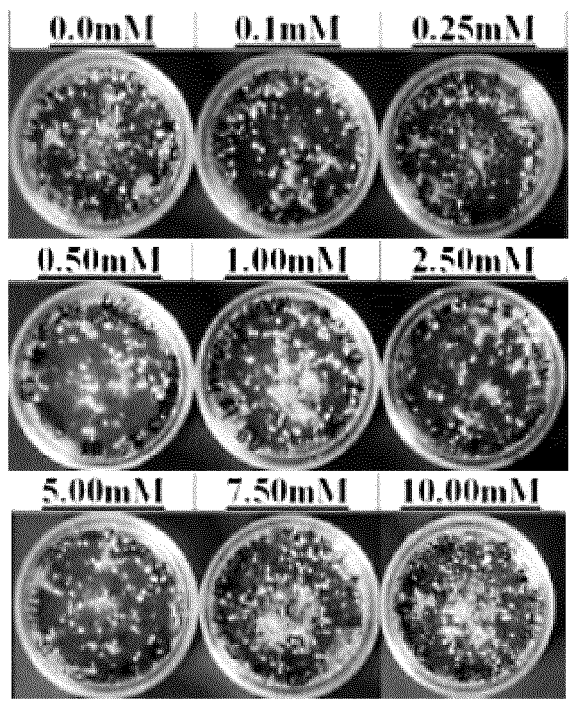
FIG. 10B is a series of photographs showing embryogenesis of triticale microspores in the presence of various concentrations of D-Ala.
Figure 10C:
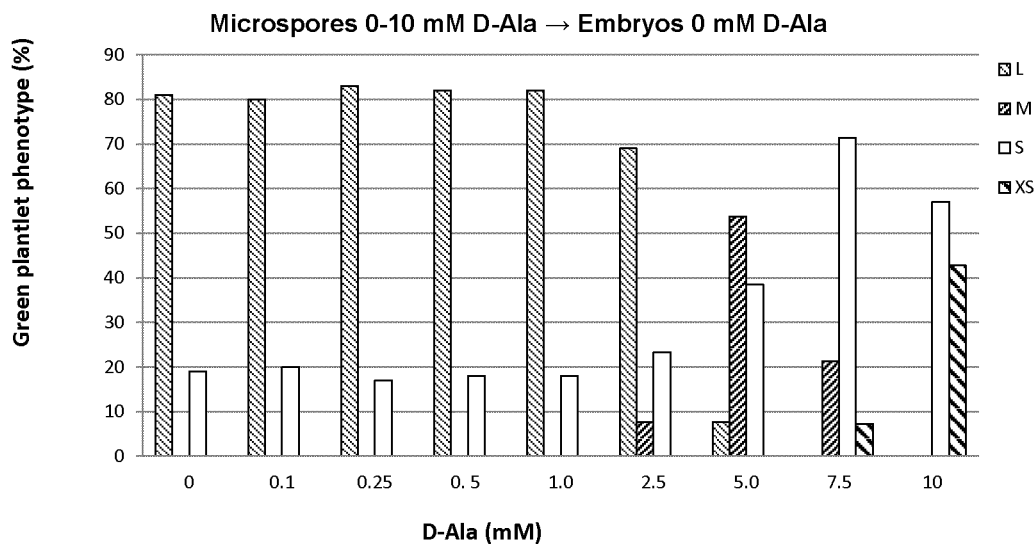
FIG. 10C is a bar graph showing the phenotype of green plantlets arising from triticale microspores cultured in the presence of various concentrations of D-Ala and transferred to germination media without D-Ala. Plantlets having a height of ≥5 cm are scored as large (L), plantlets having a height of 3-4 cm are scored as medium (M), plantlets having a height of 1-2 cm are scored as small (S), and plantlets having a height of <1 cm are scored as extra small (XS)
Figure 10D:
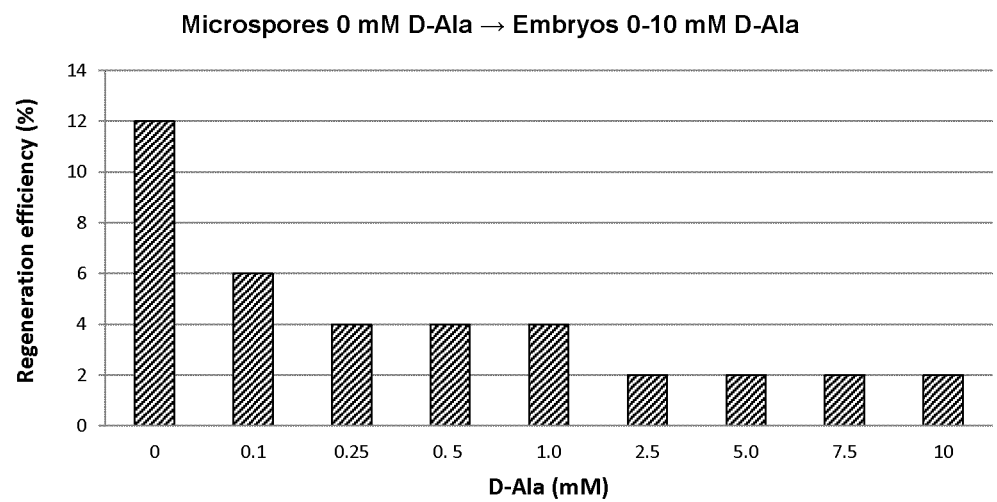
FIG. 10D is a bar graph showing the regeneration efficiency of green plantlets arising from triticale microspores cultured without D-Ala and transferred to germination media in the presence of various concentrations of D-Ala.

The effect of the selection agent D-alanine (D-Ala) on microspore viability, embryogenesis and embryo germination was tested. No noticeable effect of D-Ala at concentrations up to 10 mM on microspore viability and embryogenesis was observed, as seen from the results presented in FIGS. 10A and B. However, when embryos originated from microspores cultured in the presence of various concentrations of D-Ala were transferred to germination media without D-Ala, a reduction in the quality of the germinated green plantlets, which is dependent on the D-Ala concentration, was observed starting at 2.5 mM D-Ala, as seen in FIG. 10C, although the plant regeneration efficiency was not dramatically reduced (from 12% to 10%). Moreover, embryos developed from microspores cultured in medium without D-Ala showed a more severe reduction in the plant regeneration efficiency (from 12% to 2%), as seen from the results presented in FIG. 10D, concomitant with reduction in the quality of the germinated plantlets. Based on these findings the DAAO selection procedure for triticale was developed: 2.5 mM D-Ala for microspore culture and 5 mM D-Ala for embryo germination and plant regeneration.

The pUC_W_M_DAAO plasmid was constructed by cloning the W_M_DAAO construct (4.7 kb, FIG. 3C) into the pUC18/19 cloning vector (GeneBank #L09137). The W_M_DAAO construct carries the mitochondria codon optimized daao (D-amino acid oxidase) gene from *Saccharomyces pombe* (Gisby et al., *Plant Physiol.* (2012), 160: 2219-2226) under the control of the wheat mitochondrial promoter and terminator, flanked by 1 kb long 5'and 3' homology regions (HR). DNA containing the W_M_DAAO construct (FIG. 3C) was produced by restriction digest of the pUC_W_M_DAAO plasmid DNA with XbaI and EcoRI enzymes, followed by extraction of a 4.7 kb long DNA from agarose gel and purification using a NucleoSpin™ Gel and PCR Clean-up kit (Macherey-Nagel) according to the supplier manual.

Triticale microspores were transfected as described in Example 2 with nanocomplexes formed by mixing mTP4 and W_M_DAAO DNA at a peptide:DNA ratio of 15:1 (w:w). The daao transcript abundance in triticale microspores at 48 h after transfection was analyzed by qRT-PCR of total isolated RNA as described in Example 2. Three repetitions were used to measure the fold difference of normalized daao mRNA expression compared to the control levels of mitochondrial endogenous cob mRNA expression, using the standard curve method.

Figure 11:
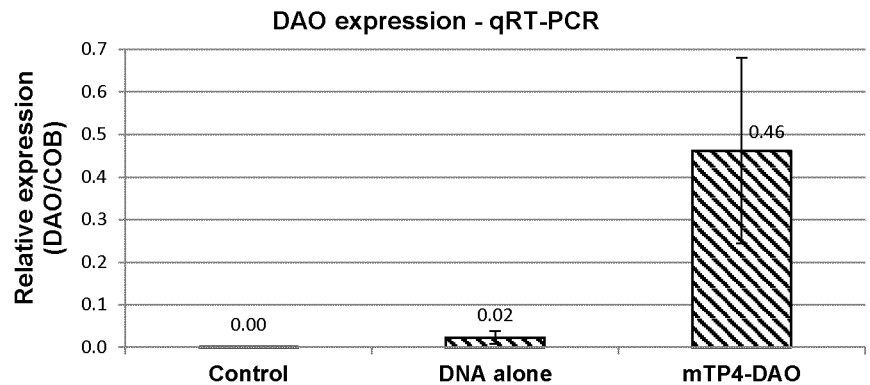
FIG. 11 is a bar graph showing the level of relative transient expression of the daao gene in triticale microspores transfected with nanocomplexes formed from mTP4 and the DNA construct of FIG. 3C (mTP4-DAO)

As seen from the results presented in FIG. 11, the daao gene transcript could be detected in transfected microspores (mTP4-DAO) 48 hours post transfection, while no daao transcript was detected in control microspores. The transfected microspores were cultured in embryo induction medium for 4 weeks with and without 2.5 mM D-Ala selection. Embryos were then transferred onto embryo germination medium containing 5 mM D-Ala to produce green plantlets. Preliminary results suggest that, although green plantlets were obtained from embryos originating from mTP4-daao-transfected microspores, the selection pressure on embryos may need to be increased.

Combined Selection

Figure 12A:
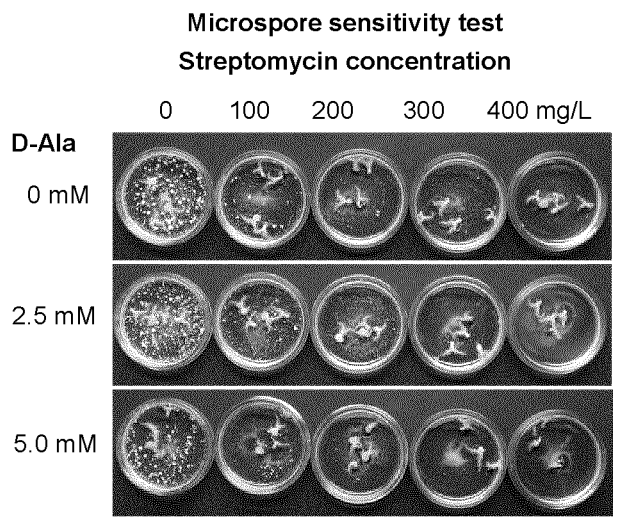
FIG. 12A is a series of photographs showing embryogenesis of triticale microspores in the presence of varying concentrations of D-Ala and streptomycin.
Figure 12B:
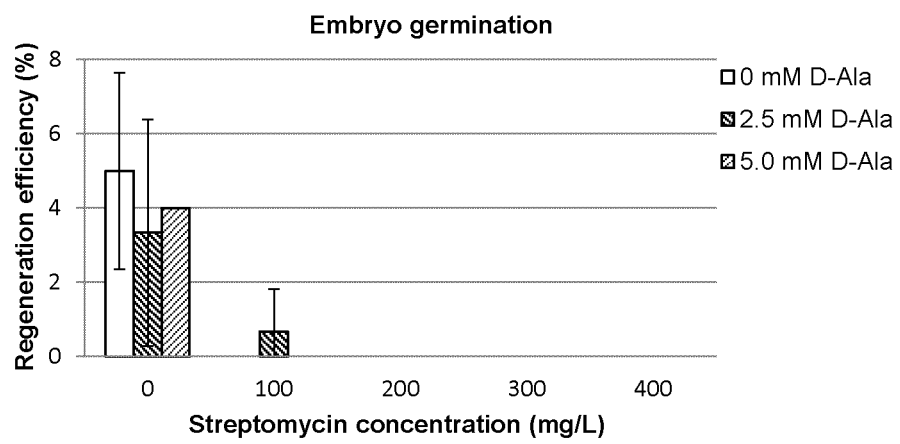
FIG. 12B is a bar graph showing the regeneration efficiency of triticale embryos exposed to varying concentrations of D-Ala and streptomycin.

Combined selection included selection for the daao marker gene as described above and selection for the aminoglycoside-3"-adenylyltransferase gene (aadA) marker gene as described by MacMillan (Plant organelle targeting cell penetration peptides. Ph.D. thesis, 2013, University of Lethbridge, Canada; MacMillan et al., Plant Biotechnology Reports, 2018, in press, DOI: 10.1007/s11816-018-0502-y). The effect of two selection agents (D-Ala and streptomycin) on microspore embryogenesis and embryo germination was tested. As seen from the results presented in FIG. 12A, the presence of 100 mg/L streptomycin significantly reduced the ability of microspores to form embryos, and higher concentrations of streptomycin (400 mg/L) resulted in complete abolishment of microspore embryogenesis. Addition of D-Ala at 2.5 mM or 5.0 mM concentration to medium containing streptomycin lower than 400 mg/L had minimal if any effect. In addition, as seen from the results presented in FIG. 12B, triticale embryos exposed to streptomycin at concentrations ≥200 mg/L, in the presence or absence of D-Ala (2.5 mM and 5 mM), were not able to regenerate into green plantlets. Based on these findings a combined selection procedure for triticale was developed: 100 mg/L streptomycin plus 2.5 mM D-Ala for microspore culture and 200 mg/L streptomycin plus 5 mM D-Ala for embryo germination and plant regeneration.

Figure 13:
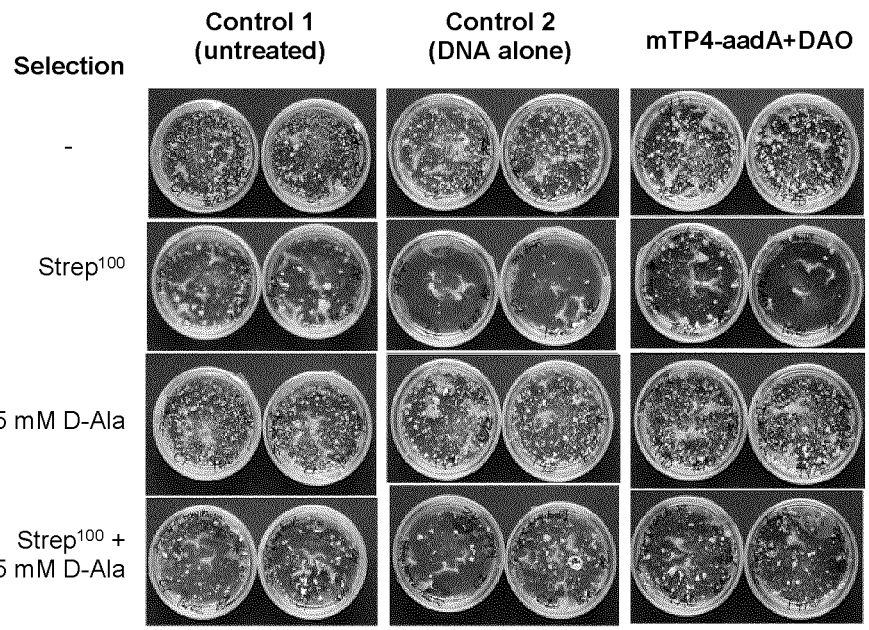
FIG. 13 is a series of photographs showing embryo development from triticale microspores transfected with nanocomplexes formed by mixing mTP4 with DNA constructs including aadA and daao genes (mTP4–aadA+DAO), with and without combined selection.

Triticale microspores were transfected with peptide-DNA complexes formed by mixing mTP4 and plasmid DNAs carrying the aadA and daao selectable marker genes at a 15:1 (w:w) peptide to DNA ratio. The transfected microspores were cultured in the embryo induction medium for 4 weeks with and without single (2.5 mM D-Ala or 100 mg/L streptomycin) or combined 2.5 mM D-Ala+100 mg/L streptomycin selection. As seen from the results presented in FIG. 13, a slightly higher number of embryos was formed from transfected microspores (mTP4–aadA+DAO) as compared to controls: untreated microspores (Control 1) and cells treated with DNA alone (Control 2). Embryos were then transferred onto embryo germination medium containing 5 mM D-Ala+200 mg/L streptomycin to produce green plantlets. Preliminary results suggest that, although green plantlets were obtained from embryos originating from mTP4–aadA+daao-transfected microspores, the selection pressure on embryos may need to be increased.

Nitrogen Deficiency Selection

Figure 14:
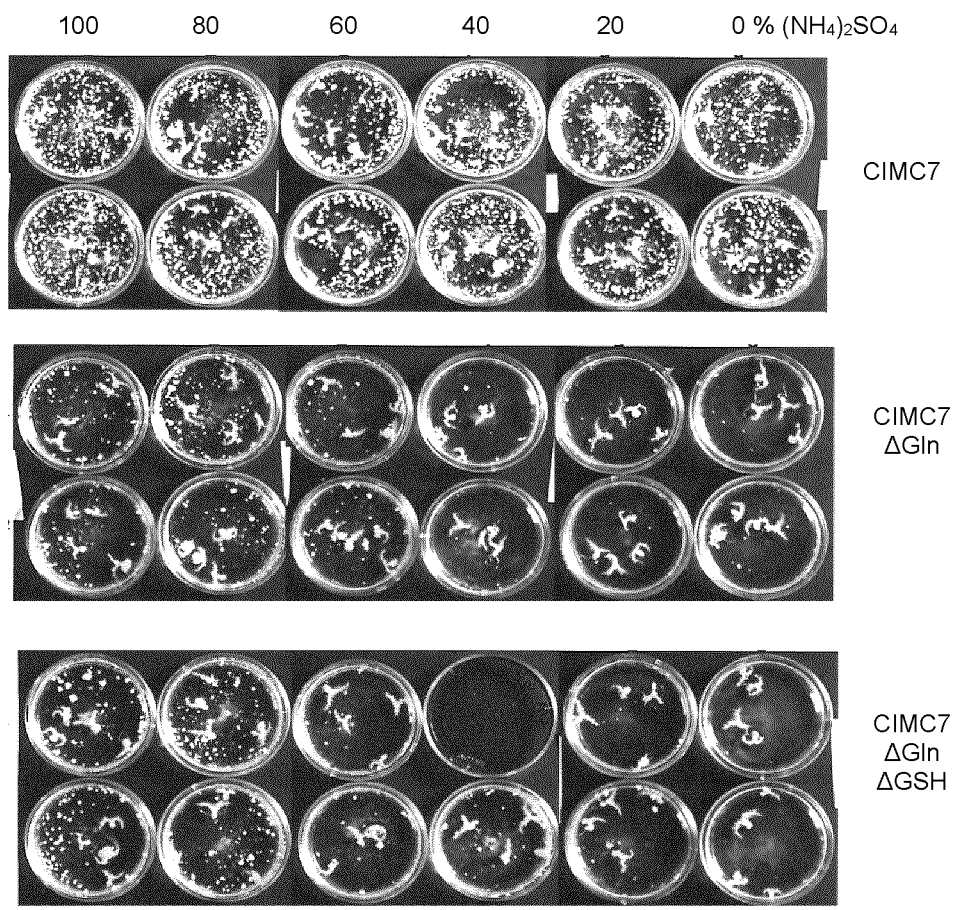
FIG. 14 is a series of photographs showing embryogenesis of triticale microspores in the presence or absence of the nitrogen sources (NH$_4$)$_2$SO$_4$ and/or glutamine (ΔGln) and glutathione (ΔGlnΔGSH).

Triticale microspores were cultured on increased repression medium (modified CIMC-7), in the presence or absence of $(NH_4)_2SO_4$ (a mineral or inorganic source of nitrogen), glutamine (ΔGln) and glutathione (ΔGlnΔGSH) (organic sources of nitrogen). The content of $(NH_4)_2SO_4$ was reduced from 100% (1.76 mM) to 80, 60, 40, 20 and 0% (1.41, 1.06, 0.7, 0.35 and 0 mM, respectively). In addition, the culture medium containing various concentrations of inorganic nitrogen was depleted of organic nitrogen sources, including the amino acid glutamine (Gln) and the peptide glutathione (GSH) which are normally present at a concentration of 3.43 mM and 3.25 nM, respectively. Omission of an inorganic nitrogen source only slightly reduced the efficiency of microspore embryogenesis, whereas lack of Gln and GSH had a dramatic effect on microspore embryogenesis, as seen from the results presented in FIG. 14. The effect of reduction in the inorganic and organic nitrogen sources on embryo germination can be tested by culturing triticale embryos on CIMC-4 standard germination medium as well as the medium containing 60, 40 or 0% $(NH_4)_2SO_4$ with or without glutamine and proline.

The embodiments described herein are intended to be illustrative of the present compositions and methods and are not intended to limit the scope of the present invention. Various modifications and changes consistent with the description as a whole and which are readily apparent to the person of skill in the art are intended to be included. The appended claims should not be limited by the specific embodiments set forth in the examples, but should be given the broadest interpretation consistent with the description as a whole.

The invention claimed is:

1. A method of transforming a mitochondrion of a plant cell to express a nitrogenase enzyme, the method comprising exposing the plant cell to a mitochondrial-targeting nanocarrier polypeptide and one or more nucleic acids, wherein the one or more nucleic acids comprise one or more genes encoding the nitrogenase enzyme, wherein the mitochondrial-targeting nanocarrier polypeptide and the one or more nucleic acids are present in a ratio by weight of about 100:1.

2. The method according to claim 1 wherein the one or more genes encoding the nitrogenase enzyme comprise one or more nif genes.

3. The method according to claim 2 wherein the one or more nif genes are genes from a species of *Klebsiella*.

4. The method according to claim 2 wherein the one or more nif genes comprise nifH, nifD and nifK.

5. The method according to claim 1 wherein the one or more nucleic acids further comprise at least one selection marker gene.

6. The method according to claim 5 wherein the selection marker gene is selected from a gene encoding aminoglycoside-3"-adenylyltransferase and a gene encoding D-amino acid oxidase.

7. The method according to claim 1 wherein the mitochondrial-targeting nanocarrier polypeptide is selected from:

MFSYLPRYPLRAASARALVRATRPSYRSALLRYQ; (SEQ ID NO: 1)

MAAWMRSLFSPLKKLWIRMH; (SEQ ID NO: 2)

MKLLWRLILSRKW; (SEQ ID NO: 3)

MWWRRSRTNSLRYT; (SEQ ID NO: 4)
and

MLFRLRRSVRLRGLLA. (SEQ ID NO: 5)

8. The method according to claim 1 wherein the plant cell is a triticale cell or a wheat cell.

9. A genetically engineered plant cell comprising a mitochondrion transformed by the method of claim 1.

10. A genetically engineered plant comprising the genetically engineered plant cell of claim 9.

11. A method of generating a genetically engineered plant, the method comprising transforming a mitochondrion of a plant cell to express a nitrogenase enzyme according to the method of claim 1, and generating the genetically engineered plant from the plant cell.

12. The method according to claim 1, wherein the mitochondrial-targeting nanocarrier polypeptide is MKLLWRLILSRKW (SEQ ID NO:3).

* * * * *

SEQUENCE LISTING

<160> NUMBER OF SEQ ID NOS: 47

<210> SEQ ID NO 1
<211> LENGTH: 34
<212> TYPE: PRT
<213> ORGANISM: Artificial Sequence
<220> FEATURE:
<223> OTHER INFORMATION: mTP1

<400> SEQUENCE: 1

Met Phe Ser Tyr Leu Pro Arg Tyr Pro Leu Arg Ala Ala Ser Ala Arg
1               5                   10                  15

Ala Leu Val Arg Ala Thr Arg Pro Ser Tyr Arg Ser Ala Leu Leu Arg
            20                  25                  30

Tyr Gln

<210> SEQ ID NO 2
<211> LENGTH: 20
<212> TYPE: PRT
<213> ORGANISM: Artificial Sequence
<220> FEATURE:
<223> OTHER INFORMATION: mTP2

<400> SEQUENCE: 2

Met Ala Ala Trp Met Arg Ser Leu Phe Ser Pro Leu Lys Lys Leu Trp
1               5                   10                  15

Ile Arg Met His
            20

<210> SEQ ID NO 3
<211> LENGTH: 13
<212> TYPE: PRT
<213> ORGANISM: Artificial Sequence
<220> FEATURE:
<223> OTHER INFORMATION: mTP3

<400> SEQUENCE: 3

Met Lys Leu Leu Trp Arg Leu Ile Leu Ser Arg Lys Trp
1               5                   10

<210> SEQ ID NO 4
<211> LENGTH: 14
<212> TYPE: PRT
<213> ORGANISM: Artificial Sequence
<220> FEATURE:
<223> OTHER INFORMATION: mTP4

<400> SEQUENCE: 4

Met Trp Trp Arg Arg Ser Arg Thr Asn Ser Leu Arg Tyr Thr
1               5                   10

<210> SEQ ID NO 5
<211> LENGTH: 16
<212> TYPE: PRT
<213> ORGANISM: Artificial Sequence
<220> FEATURE:
<223> OTHER INFORMATION: mTP5

<400> SEQUENCE: 5

Met Leu Phe Arg Leu Arg Arg Ser Val Arg Leu Arg Gly Leu Leu Ala
1               5                   10                  15

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
cacatgggtc tggtcaggaa                                         20

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
cgaggacctt tatagccata attca                                                 25

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ctgctgaagt gggatccgtt                                                       20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ctcgtccagc acatccaaca                                                       20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
tgactgttcg tggatgtgct                                                       20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
ccacaccaga aacaccggta                                                       20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
tgcttggact actaccgctg                                                       20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
gcaacacatc cttgggatcc                                                       20

<210> SEQ ID NO 14
<211> LENGTH: 20
<212> TYPE: DNA
<213> ORGANISM: Artificial Sequence -continued

```
<220> FEATURE:
<223> OTHER INFORMATION: Primer

<400> SEQUENCE: 14
tgcttggact actaccgctg                                           20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
gcaacacatc cttgggatcc                                           20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
atcatgcagc cagaacagct                                           20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
acaagctgga gcaacaggaa                                           20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
ctcctcgaga ttggcaagct                                           20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
aggtccagca tcttgttgca                                           20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
acccgatatc atcctgctgc                                           20
```

```
<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
atcacatcac cagcaggacg                                               20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
cctgctgatc ttttggtggc                                               20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
tccttgacga acacgacgaa                                               20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
tctgctcgtg gtgctcaaat                                               20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
agccaagaag caagacgagc                                               20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
tggaactgct gcttgggaaa                                               20

<210> SEQ ID NO 27
<211> LENGTH: 20
<212> TYPE: DNA
<213> ORGANISM: Artificial Sequence
<220> FEATURE:
<223> OTHER INFORMATION: Primer
```

<400> SEQUENCE: 27
agagcaggac gaatagcagc						20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
ctcctgctgt tgcttctgga						20

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
ccagacaaag acacggtcac t						21

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
gggtgctgct tgtgaattgg						20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
caggaacagc aggttgtcca						20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
aggattggga gaacgtgctg						20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
gccacacgtt gacaagaagc						20

<210> SEQ ID NO 34

<211> LENGTH: 21
<212> TYPE: DNA
<213> ORGANISM: Artificial Sequence
<220> FEATURE:
<223> OTHER INFORMATION: Primer

<400> SEQUENCE: 34
tgatgaactt cgatccgctg a        21

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
aagaggcact tcagcacgaa           20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
tcaaccatgg cttgctggaa           20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
acagaaaacc aacgaccgga           20

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
gctcgtgttc ctgaaggtga           20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
ctggttgagg agcttgtcga           20

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
agaatggcat ggatcggtag                                    20

<210> SEQ ID NO 41
<211> LENGTH: 19
<212> TYPE: DNA
<213> ORGANISM: Artificial Sequence
<220> FEATURE:
<223> OTHER INFORMATION: Primer

<400> SEQUENCE: 41
tcctaatgtt ttgggcatc                                     19

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
ttccacgaat ctcactgcac                                    20

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
gttgggctgt accttcctca                                    20

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
gtaagggcga tccatcttga                                    20

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
gggaattgaa gagggagaa                                     20

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
gaattgttcc acggcaaggg                                    20

<210> SEQ ID NO 47
<211> LENGTH: 20
<212> TYPE: DNA

```
<213> ORGANISM: Artificial Sequence
<220> FEATURE:
<223> OTHER INFORMATION: Primer

<400> SEQUENCE: 47
cagcttggta tcctgtgcca                                                    20
```